(12) United States Patent
Celenk et al.

(10) Patent No.: US 10,722,115 B2
(45) Date of Patent: Jul. 28, 2020

(54) DEVICES AND METHODS FOR CLASSIFYING DIABETIC AND MACULAR DEGENERATION

(71) Applicant: Ohio University, Athens, OH (US)

(72) Inventors: Mehmet Celenk, Athens, OH (US); H. Bryan Riley, Athens, OH (US); Nikita Gurudath, Athens, OH (US); Frank Schwartz, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 15/751,947

(22) PCT Filed: Aug. 16, 2016

(86) PCT No.: PCT/US2016/047132
§ 371 (c)(1),
(2) Date: Feb. 12, 2018

(87) PCT Pub. No.: WO2017/031099
PCT Pub. Date: Feb. 23, 2017

(65) Prior Publication Data
US 2018/0235467 A1 Aug. 23, 2018

Related U.S. Application Data

(60) Provisional application No. 62/207,626, filed on Aug. 20, 2015.

(51) Int. Cl.
| | |
|---|---|
| *A61B 3/12* | (2006.01) |
| *A61B 3/14* | (2006.01) |
| *G06K 9/00* | (2006.01) |
| *G06K 9/46* | (2006.01) |
| *G06T 7/00* | (2017.01) |

(52) U.S. Cl.
CPC .............. *A61B 3/1241* (2013.01); *A61B 3/14* (2013.01); *G06K 9/0061* (2013.01); *G06K 9/00617* (2013.01); *G06K 9/46* (2013.01); *G06T 7/0012* (2013.01); *G06K 2209/05* (2013.01); *G06T 2207/10024* (2013.01); *G06T 2207/20084* (2013.01); *G06T 2207/30041* (2013.01); *G06T 2207/30101* (2013.01)

(58) Field of Classification Search
CPC ........... A61B 3/14; A61B 3/0025; A61B 3/12; A61B 3/102; A61B 3/0058
USPC ........................................................ 351/206
See application file for complete search history.

(56) References Cited

U.S. PATENT DOCUMENTS

| | | | | |
|---|---|---|---|---|
| 8,879,813 B1 * | 11/2014 | Solanki | ............... | G16H 30/20 382/128 |
| 9,462,945 B1 * | 10/2016 | Barriga | ............... | A61B 3/152 |
| 2012/0150029 A1 * | 6/2012 | Debuc | ............... | A61B 3/102 600/425 |

FOREIGN PATENT DOCUMENTS

EP 2827298 A1 * 1/2015 ............... G06T 7/12

* cited by examiner

*Primary Examiner* — Mohammed A Hasan
(74) *Attorney, Agent, or Firm* — MacMillan, Sobanski & Todd, LLC

(57) ABSTRACT

Devices and methods for determining a propensity to diabetic and/or macular degeneration in a subject by measuring certain featured from a captured retinal image from a subject are described.

13 Claims, 33 Drawing Sheets
(18 of 33 Drawing Sheet(s) Filed in Color)

DEVICES AND METHODS FOR CLASSIFYING DIABETIC AND MACULAR DEGENERATION

CROSS-REFERENCE TO RELATED APPLICATIONS

This application is a national stage application filed under 35 U.S.C. § 371 of international application PCT/US2016/047132, filed under the authority of the Patent Cooperation Treaty on Aug. 16, 2016, which claims the priority to U.S. Provisional Application Ser. No. 62/207,626, filed Aug. 20, 2015, the entire disclosure of which is expressly incorporated herein by reference.

TECHNICAL FIELD

This invention relates to a computer-assisted technology for diseases diagnosis. In a particular aspect, it relates to a computer-assisted device and method for non-invasive diabetic retinopathy detection, classification, and monitoring.

STATEMENT REGARDING FEDERALLY FUNDED SPONSORED RESEARCH

This invention not was made with any government support and the U. S. government has no rights in the invention.

BACKGROUND OF THE INVENTION

Diabetes mellitus affects nearly 26 million US adults with 1.5 million more cases diagnosed each year as noted by Centers for Disease Control and Prevention (CDC) in 2011. The CDC predicts that 1 in 3 Americans born in 2000 will develop diabetes in their lifetime. Diabetes is associated with multiple long term complications including premature cardiovascular disease, chronic kidney disease and diabetic retinopathy. Diabetic retinopathy and macular edema are the leading cause of new blindness diagnoses in the US. While millions of Americans have been diagnosed with diabetic and/or macular degeneration, a serious problem is that many more are unaware they are at high risk. One-third to one-half of people with diabetic and/or macular degeneration are undiagnosed and, hence, untreated. Although it has been shown that aggressive lifestyle intervention can delay or prevent diabetic and/or macular degeneration in those at high risk, it is also believed that earlier diagnosis and specific treatment of the eye disease either through laser photocoagulation or use of medications which block abnormal retinal vessel growth can prevent or delay the serious complications related to the disease (blindness) and improve health outcomes significantly. Since one third of people have a complication from diabetic retinopathy and/or macular degeneration at the time of diagnosis and duration of hyperglycemia is directly related to complications, earlier detection and intervention could have a significant impact on complication prevention.

In spite of considerable research into new methods to diagnose and treat this disease, diabetes remains difficult to treat effectively, and the mortality observed in patients indicates that improvements are needed in the diagnosis, treatment and prevention of this disease. There are multiple social and economic barriers to access to health care providers in the US and world-wide for earlier diagnosis and treatment and there is also a need for an improved approach to screen and classify the risk for future complications such as blindness from diabetes by utilizing new mobile technologies.

SUMMARY OF THE INVENTION

In a first broad aspect, there is described herein a detection system to detect and classify the severity of diabetic retinopathy and macular degeneration.

A method for determining whether a subject has diabetic and/or macular degeneration, or a pre-disposition for developing diabetic and/or macular degeneration, wherein the method comprises the steps of:

determining the presence or absence of a set of features in at least one digital retinal image taken of the subject by:

i) creating an edge profile map of the fundus images that detects the retinal vasculature and one or more abnormalities characteristic of the stage of retinopathy based on an adaptive mask generation procedure; and specifically the design and implementation of the adaptive mask.

ii) classifying the processed images using features which describe the texture and shape via artificial neural network (ANN) and support vector machines (SVM);

and, based on the presence or absence of such set of features, determining whether the subject has diabetic and/or macular degeneration, or a pre-disposition for developing diabetic and/or macular degeneration;

optionally, recommending a particular treatment for diabetic and/or macular degeneration or pre-diabetic and/or macular degeneration condition.

Various objects and advantages of this invention are apparent to those skilled in the art (i.e., machine learning—specifically ANNs and SVNs) from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION OF THE PREFERRED EMBODIMENT(S)

Figure 1:
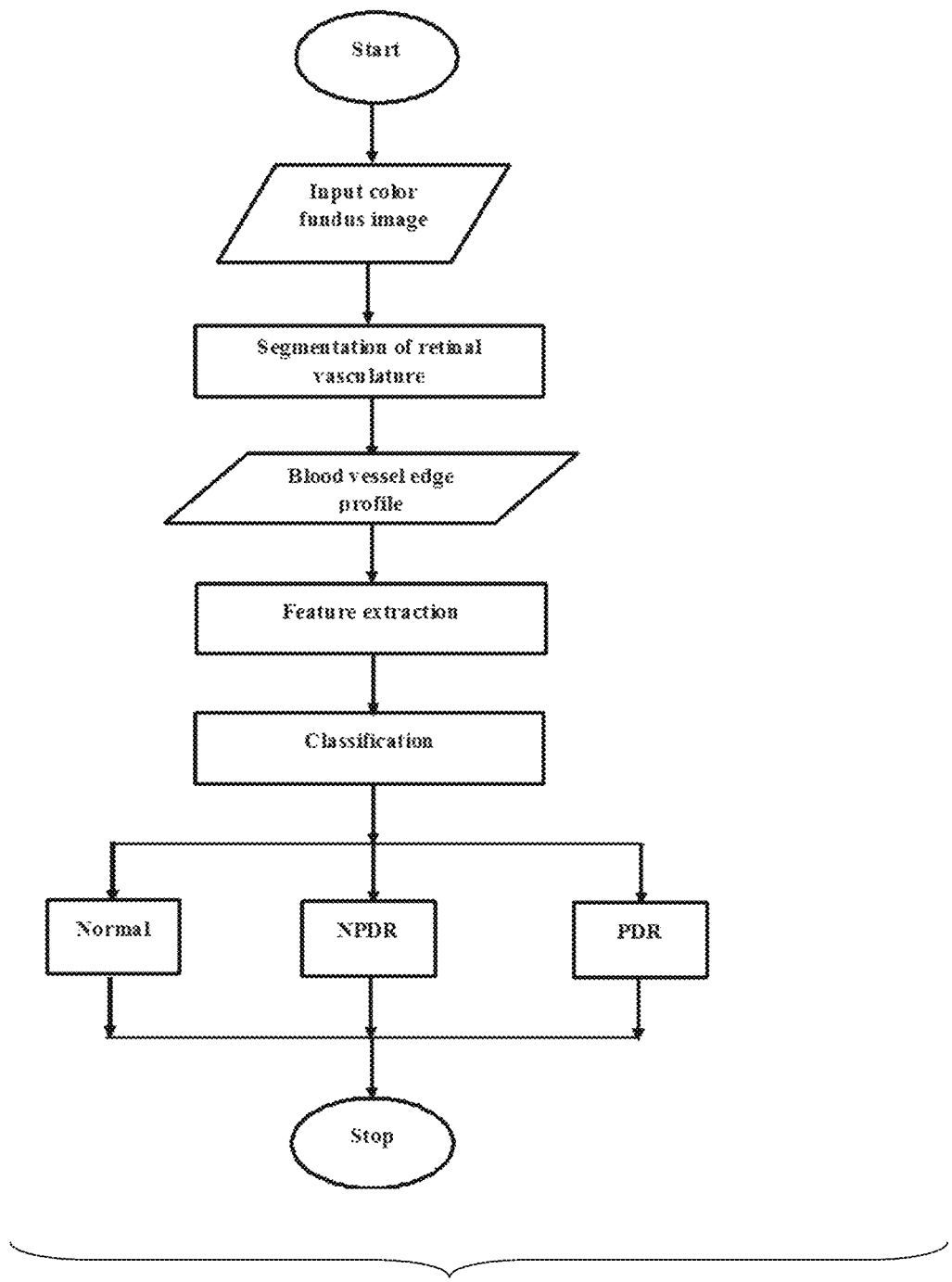
FIG. 1. Flow diagram showing high process flow of one embodiment.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

In order to facilitate review of the various embodiments of the disclosure, the following explanations of specific terms are provided:

Prediabetes: A condition of abnormal glucose regulations (impaired fasting glucose or impaired glucose tolerance) that is above normal but not diagnostic of diabetes.

Type 1 diabetes (TIDM): Formerly termed Insulin-Dependent DM (IDDM) or juvenile diabetes). An autoimmune condition in which the insulin producing beta cells of the pancreas are destroyed, resulting in a subject not secreting sufficient insulin and therefore needing exogenous insulin to live.

Type 2 diabetes (diabetic and/or macular degeneration): Formerly termed Non-Insulin-Dependent DM (NIDDM) or adult-onset diabetes). A condition that results from genetic abnormalities combined with environmental and lifestyle risks that result in abnormal glucose values that result from insulin resistance, abnormal glucose production from the liver, or impaired insulin secretion.

Therapeutic: A generic term that includes both diagnosis and treatment. It will be appreciated that in these methods the "therapy" may be any therapy for treating a disease including, but not limited to, pharmaceutical compositions, gene therapy and biologic therapy such as the administering of antibodies and chemokines. Thus, the methods described herein may be used to evaluate a patient before, during and after therapy, for example, to evaluate the reduction in disease state.

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Patient: As used herein, the term "patient" includes human and non-human animals. The preferred patient for treatment is a human. "Patient," "individual" and "subject" are used interchangeably herein.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Poor prognosis: Generally refers to a decrease in survival, or in other words, an increase in risk of death or a decrease in the time until death. Poor prognosis can also refer to an increase in severity of the disease, such as an increase in spread (metastasis) of the cancer to other tissues and/or organs.

Screening: As used herein, "screening" refers to the process used to evaluate and identify candidate agents that affect such disease.

General Description

Described herein is an easily useable screening or detection system that identifies individuals predisposed to develop diabetic and/or macular degeneration.

Described herein are devices that can use a portable retinal camera and a PC-based system to diagnose diabetic retinopathy, which is classically diagnosed and staged by physicians who are specifically trained to diagnose and treat eye disease.

The device is portable and can be used by non-professionals trained to perform a "near-clinical analysis" of patient retinas, and report a diagnosis that characterizes the stage or progression of diabetic retinopathy.

The system and device enables access to individuals in physician offices or can be used for screening in remote/rural areas of the world without comprehensive health care systems and provide the ability to detect retinopathy earlier and then capacity to refer individuals to specialized care (to persons living in underprivileged areas with limited health in both this nation and worldwide). Further, optometrists and ophthalmologists can also benefit from this technology to screen patients, detect retinal disease earlier and then intervene with appropriate treatment.

In clinical examination, eye care professionals examine the retina directly as well with digital photographs for early signs of the disease including: leaking blood vessels; retinal swelling such as macular edema; pale, fatty deposits on the retina, namely, exudates, as signs of leaking blood vessels; damaged nerve tissue (i.e., neuropathy); and/or, and changes in the blood vessels.

The system and device described herein provide information about the existence of these abnormalities in the processed digital retinal images are described in this patent provision. This enhanced image guides the eye examiner with greater efficiency and confidence regarding the state of health of a patient's retina. Thus the device described herein, allows for highly informative and reliable clinical conclusions with 98% detection and classification accuracy as compared to the existing system which reports 96% classification accuracy.

The system and device described herein provide a method to identify the presence of diabetic retinopathy from digital color fundus images of the human retina. The method generally includes the steps of: segmentation of retinal vasculature, feature extraction, and classification. In particular, the method starts with the classification of an input fundus image. The classification is defined in terms three distinct classes: Healthy and normal eye; Non-Proliferative Diabetic Retinopathy (NPDR); and, Proliferative Diabetic Retinopathy (PDR). The next step is blood vessel segmentation of the input image, which can be achieved by Gaussian filtering. The Gaussian filter or smoothing function used an N-dimensional convolution operator that is applied to primarily remove non-essential details and noise. The Gaussian filtering uses a "kernel" to represents the shape of a Gaussian or bell-shape curve. As a result, an intensity profile can be generated from a single retinal image.

Figure 11:
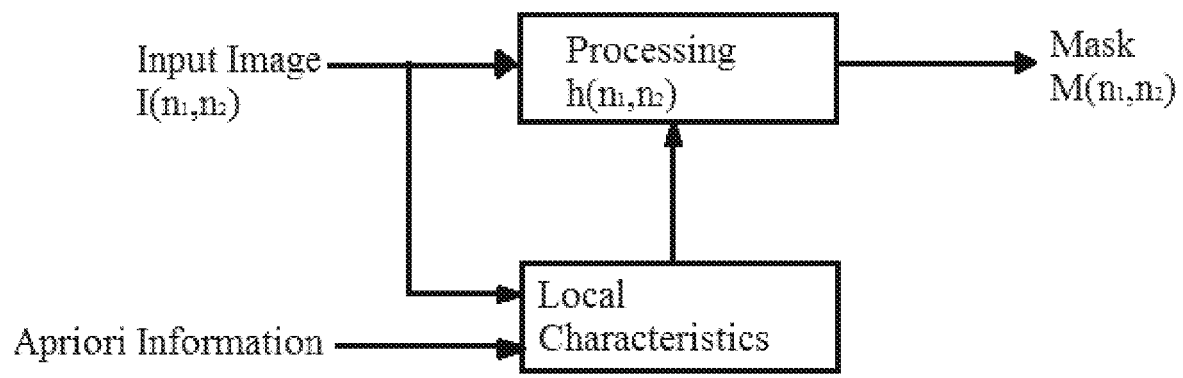
FIG. 11. General adaptive image processing system to generate the mask.

The resulting image, denoted as $I_g(n_1, n_2)$ is subjected to a local thresholding scheme based on entropy, and a mask $M(n_1, n_2)$ is generated in order to define the Region of Interest (ROI) for application of thresholding. The mask generated is a linear convolution between the system impulse response and the input grayscale image. The mask is determined depending on the grayscale input image, $I(n_1, n_2)$. (A block diagram implementation depicting the adaptive mask is generation process is shown in FIG. 11).

This adaptive, input-driven approach is considered for the mask generation and thresholding is accomplished using local entropy.

Feature extraction is performed on the image after thresholding, $I_t(n_1, n_2)$. The fundus images are appropriately prepared and as such classification now requires surface inspection.

Textures of images provide information about the spatial distribution of gray levels that is integral to defining the regions in fundus images that contain abnormalities. In the classification step, artificial neural networks (ANN) and support vector machines (SVM) are used.

The set of features used for classification on the original and process images into one of the three (3) aforementioned claims (i.e., health/normal, NPDR or PDR) are: 1) Contrast in 0°; 2) Contrast in 45°; 3) Contrast in 90°; 4) Contrast in 135°; 5) Fractal dimension; 6) Lacunarity considering foreground pixels; and, 7) Lacunarity considering foreground pixels and empty spaces.

A three layer, feed-forward artificial neural network is selected to implement classification using the back propagation training algorithm.

The processed image obtained is characterized by second order textural feature, contrast (in four preselected degree orientations, that is, 0°, 45°, 90° and 135°), and important structural features, namely, fractal dimension and lacunarity). Thus, the method incorporated a three-layered artificial neural network to classify the retinal images. The results are obtained for original color fundus by implementing three classes overlaid by the processed images.

Using machine learning computing techniques, digital photographs are manipulated to subtract interfering pixels and allow enhanced visualization of retinal blood vessels without the use of injected, florescent dyes to noninvasively detect and stage diabetic retinopathy which is a progressive disease. The device provides over 98% classification accuracy for discriminating normal Diabetic Retinopathy (DR), Proliferative Diabetic Retinopathy (PDR) and Non-Proliferative Diabetic Retinopathy (NPDR) patient retinal using only 3-features (co-occurrence contrast measures in 0° and 90° along with lacunarity measure—gap or hole distribution/fractal of retina texture) of patient fundus images extracted automatically in real time by system with no human intervention.

The high classification accuracy stems from its adaptive Gaussian or normal-density filter construction ability in local image areas, as opposed to the commonly used practice of global (entire image) filter in the existing methods.

The device/method described herein eliminates an expensive and time-intensive processing stage. Specifically, there is no longer a need to refer to an image database system of diabetic patient fundus images (i.e., progression history) for discriminating DR, PDR, and NPDR cases.

This device/method allows for the overall diabetic retinopathy diagnostic process to be highly robust and invariant of changes in measurement or application related perturbations and conditions as opposed to the existing methods.

This device/method is also useful to diagnose or stage other diseases of the retina, such as macular edema. Further, this device/method can be used to not only stage diabetic retinopathy, but also identify characteristic patterns which could be used to predict future risk of developing a vitreous hemorrhage or retinal detachment which are major causes of blindness in diabetes.

The device/method is also useful as a teaching tool for ophthalmology residents to learn how to envision and stage diabetic retinopathy; and to diagnose other diseases of the retina such as infection, inflammatory diseases, and malignancies.

In particular, the device/method identifies the presence of diabetic retinopathy from the color fundus images of the patient retinas. Retinal vasculature is first segmented from the color images by means of matched filtering. Intensity profile of retinal blood vessels is approximated by 2D Gaussian kernel in accordance with the clinical findings. The gray level co-occurrence matrix is constructed for four different orientations of 0°, 45°, 90° and 135° and the second order statistic contrast is calculated for each of these selected directions. The fractal dimension using box count method and lacunarity was computed for the entire retinal image. A neural network (NN) of three layers is devised to classify a retinal image into one of the three classes of normal, non-proliferative diabetic retinopathy and proliferative diabetic retinopathy.

Diabetic retinopathy is characterized by neovascularization of small retinal vessels in response to metabolic derangements in the retina caused by diabetes. These abnormal vessels are very fragile and susceptible to occlusion leading to hypoxia and even more abnormal vessel formation (micro aneurysms). These abnormal vessels also leak fluid and proteins into the retinal nerve tissue itself which is visualized in the digital photographs as exudates. Based on severity, it is classified into: Non-Proliferative Diabetic Retinopathy (NPDR) and Proliferative Diabetic Retinopathy (PDR). There has been extensive research pertaining to the classification of diabetic retinopathy using image processing techniques such as thresholding, mathematical morphology and filtering, blood vessel segmentation for classification of diabetic retinopathy. Existing methods in the literature show diabetes identification rate of 91%.

Figure 2:
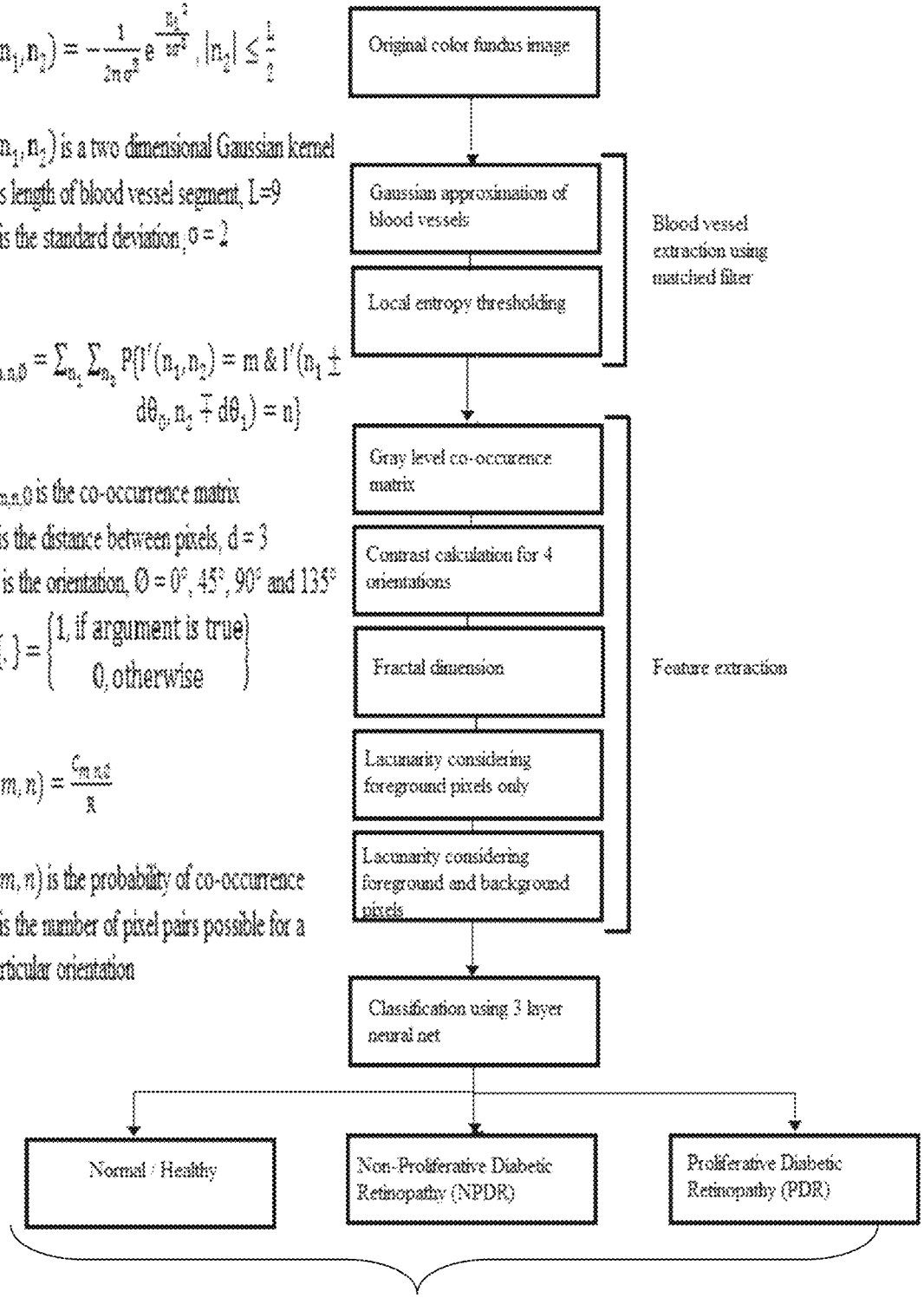
FIG. 2. Flow diagram showing suitable calculations.
Figure 3:
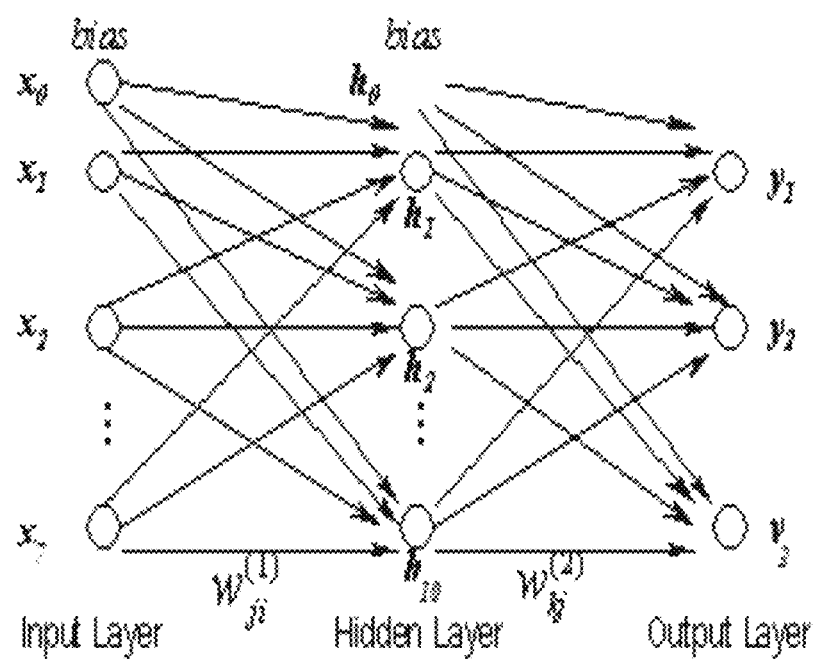
FIG. 3. Schematic illustration of the classification done using both, original color fundus images and processed images.

FIG. 1 and FIG. 2 provide schematic illustrations of general flow diagrams. FIG. 3 is a schematic illustration of the classification done using both, original color fundus images and processed images.

Figure 4A:
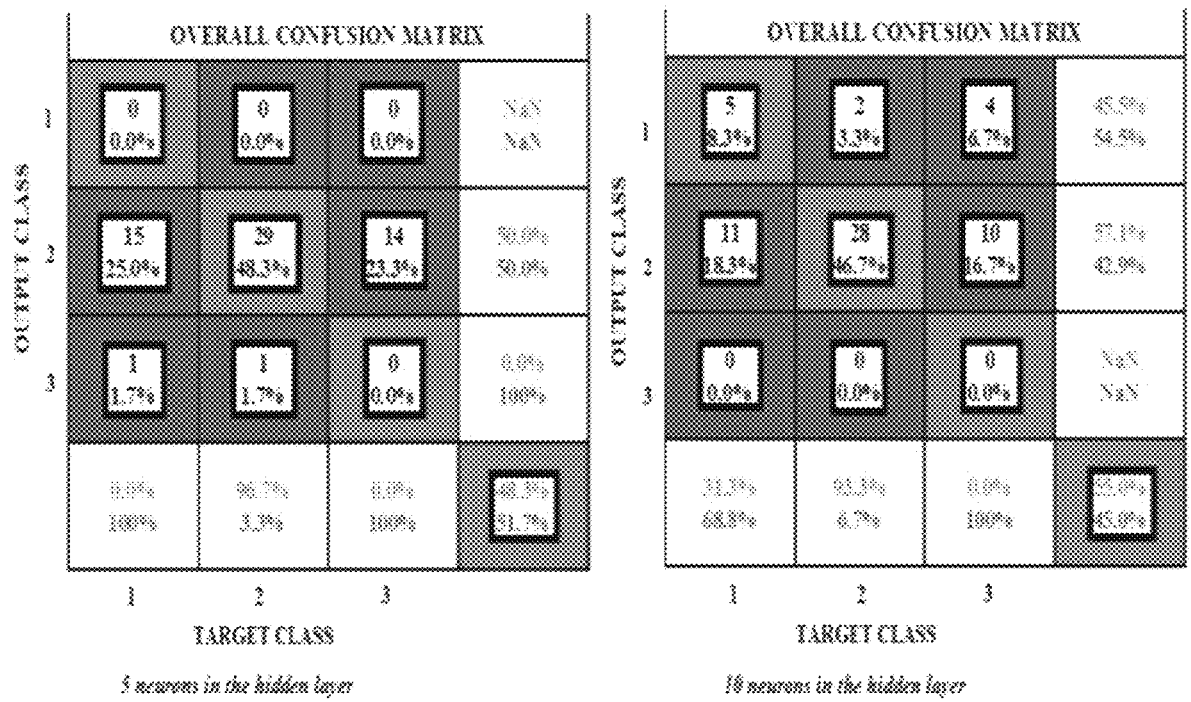
FIGS. 4A-4B. Confusion matrix for classification using 5 neurons and 10 neurons in the hidden layer: original images (FIG. 4a), and processed images (FIG. 4b).
Figure 4B:
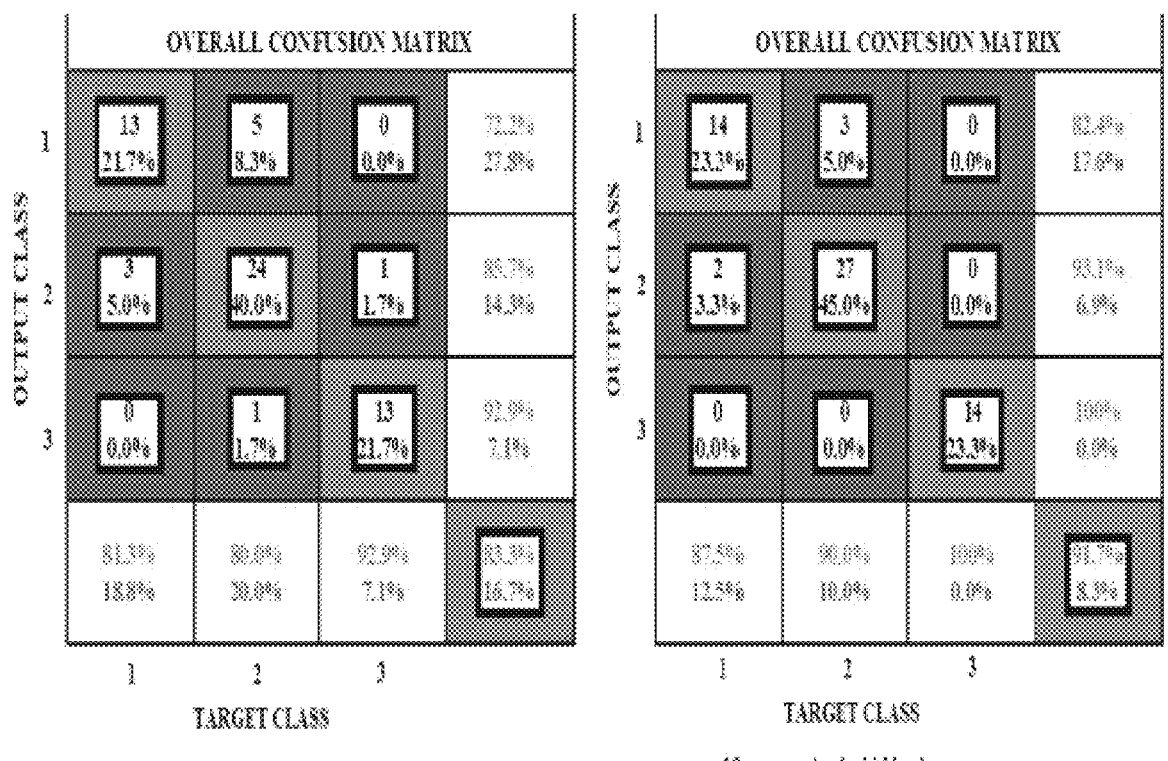

FIGS. 4A-4B illustrate a confusion matrix for classification using 5 neurons and 10 neurons in the hidden layer: original images (FIG. 4A), and processed images (FIG. 4B).

The processed image textural attributes give the descriptive information that aids in robust classification, whereas the shape features emphasize the severity of the disease. Using a combination of these two descriptors, a classification accuracy of 91.7% is obtained with a three-layer neural network.

Segmentation of Retinal Vasculature

Figure 5:
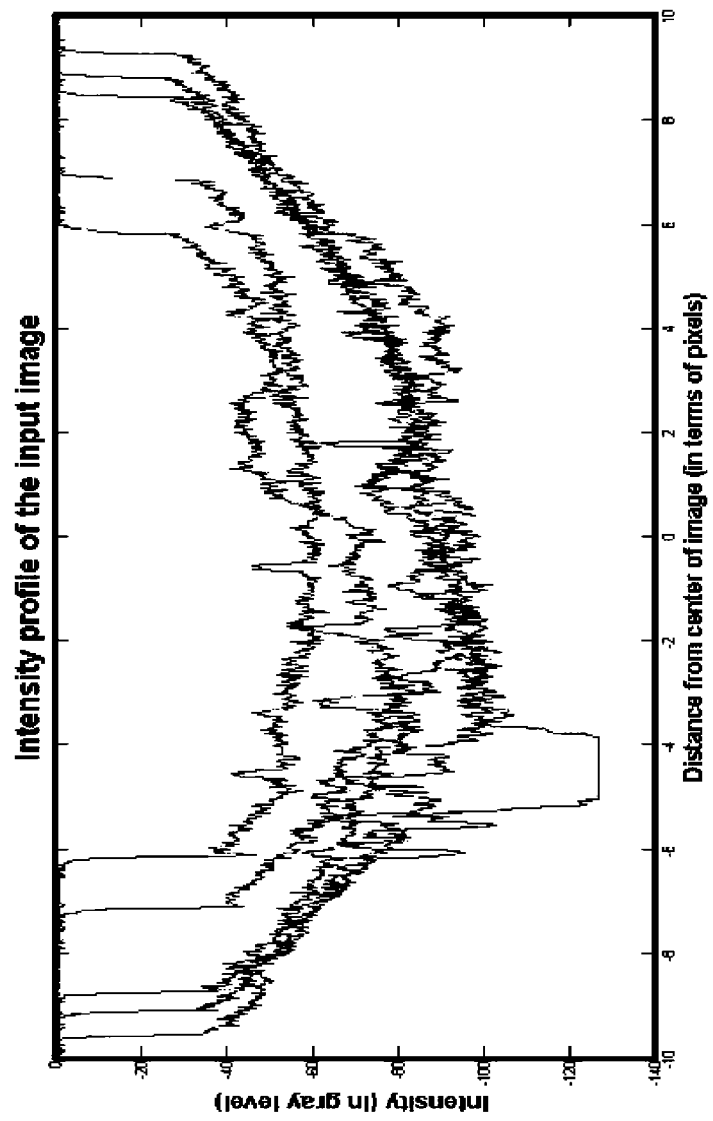
FIG. 5. Intensity profile of an input fundus image.

The blood vessels in a fundus image have lower reflectance compared to the other retinal surfaces. Hence, they appear darker than the background. Blood vessels have a tapering structure towards the edges. It is now believed that this change in blood vessels is gradual and a uniform width is considered. Gaussian distributions utilized in matched filter techniques effectively depict the grayscale profile of blood vessels. The intensity profile generated from a grayscale retinal image is illustrated in FIG. 5.

The intensity profile is instrumental in modelling the kernel function for filtering. Based on the information from FIG. 5, a Gaussian kernel is chosen as a smoothing function. The kernel aids in segregating the vessel edge from its background.

In the most general form, an N-dimensional kernel can be represented in the $X=[x_1, x_2, \ldots x_N]^T$—Cartesian coordinate system as $$G(x_1, x_2, \ldots, x_N) = \frac{1}{(2\pi)^{M/2}|\Sigma|^{1/2}} e^{\left(\frac{-1}{2}(\overline{X}-\overline{\mu})^T \cdot \Sigma^{-1} \cdot (\overline{X}-\overline{\mu})\right)} \quad (1)$$

where $\overline{\mu}=[\mu_1, \mu_2, \ldots \mu_N]^T$ is the man vector, $\Sigma$ is the positive definite N×N covariance matrix of the form $$\Sigma = \begin{bmatrix} \sigma_1^2 & \sigma_{12} & \ldots & \sigma_{1N} \\ \sigma_{21} & \sigma_2^2 & \ldots & \sigma_{2N} \\ \sigma_{N1} & \sigma_{N2} & \ldots & \sigma_N^2 \end{bmatrix},$$

$|\Sigma|$ is the determinant of positive definite N×N covariance matrix and T represents matrix transposition. Herein, a two-dimensional normal distribution in the $(n_1, n_2)$ image phase is considered. It is given by $$X(n_1, n_2) = \frac{1}{(2\pi)^{2/2}|\Sigma|^{1/2}} e^{\left(\frac{1}{2}(\overline{X}-\overline{\mu})^T \cdot \Sigma^{-1}(\overline{X}-\overline{\mu})\right)} \quad (2)$$

If the coordinate axes are uncorrelated, a two-dimensional Gaussian kernel can be defined as a product of two one-dimensional kernels defined by $$G(n_1, n_2) = -\frac{1}{\sqrt{2\pi}\,\sigma_1} e^{\left(\frac{n_1^2}{2\sigma_1^2}\right)} \cdot \frac{1}{\sqrt{2\pi}\,\sigma_2} e^{\left(\frac{n_2^2}{2\sigma_2^2}\right)} \quad (3)$$

where σ1=σ2=σ is the spread of the intensity profile. If the length of a blood vessel segment (L) is assumed to be along the $n_2$ axis, then eqn. 3 can be rewritten as $$G(n_1, n_2) = -\frac{1}{2\pi\sigma^2} e^{\frac{n_1^2}{2\sigma^2}}, |n_2| \leq \frac{L}{2} \quad (4)$$

Since blood vessels are oriented arbitrarily, the kernel must be rotated in all possible directions. The angular resolution Θ determines the number of kernels (N) required, which is given by $$N = \frac{360}{\theta} \quad (5)$$

N number of kernels are convolved with the original image $I(n_1, n_2)$ of size N1×N2, and at each pixel $(n_1, n_2)$ only the maximum response is elicited. The resulting grayscale image $I_g(n_1, n_2)$ is subjected to a local thresholding scheme based on entropy.

Entropy based thresholding provides a more accurate method of thresholding since it takes into account the spatial distribution of pixels.

The first step in this thresholding approach is to calculate Haralick's matrix or gray level co-occurrence matrix defined in eqn. 6.

$$C_{m,n\Theta} = \Sigma_{n_1}\Sigma_{n_2} P\{I(n_1,n_2)=m \& I(n_1 \pm d\theta_0, n_2 \mp d\theta_1)=n\} \quad (6)$$

where d is the distance between the pixels, Ø is the orientation and $$P\{\cdot\} = \begin{Bmatrix} 1, & \text{if argument is true} \\ 0, & \text{otherwise} \end{Bmatrix}.$$

The size of $C_{m,n\emptyset}$ is the same as that of the image $I_g(n_1, n_2)$ which is specified to be N1×N2. Table 1 indicates the possible values of 0s and 01 for different orientations and for d=3.

TABLE 1 values of $\theta_0$ and $\theta_1$ for Various $\emptyset$

| $\emptyset$ | $\theta_0$ | $\theta_1$ |
|---|---|---|
| 0° | 0 | 3 |
| 45° | −3 | 3 |
| 90° | 3 | 0 |
| 135° | 3 | −3 |

If R denotes the number of pixel pairs possible for a particular orientation, then the probability of co-occurrence is given as $$P(m, n) = \frac{C_{m,n,\phi}}{R} \quad (7)$$

In this type of thresholding, the foreground and the background pixels are considered as different sources. If $0 \le T \le N-1$, then entropy for foreground pixels expressed in terms of the probability of co-occurrence is $$H_f^{(2)} = \sum_{i=0}^{T} \sum_{j=0}^{T} P(i, j) \log_2\left(\frac{1}{p(i, j)}\right) \quad (8)$$

Similarly, the entropy for background pixels is $$H_b^{(2)} = \sum_{i=T+1}^{N-1} \sum_{j=T+1}^{N-1} P(i, j) \log_2\left(\frac{1}{p(i, j)}\right) \quad (9)$$

where the superscript indicates that the measure of entropy is a second order statistic. The optimum threshold $T_{opt}$ formulated as $$T_{opt} = \text{argmax}[H_f^{(2)} + H_b^{(2)}] \quad (10)$$

Feature Extraction

Feature extraction is performed on the image obtained after thresholding $I(n_1, n_2)$. The three features extracted are second order statistic contrast in four orientations, fractal dimension and two values of lacunarity.

a) Contrast

The co-occurrence matrix is calculated for $I(n_1, n_2)$ as described by eqns. 6 and 7. For an orientation $\emptyset=\{0°, 45°, 90° \text{ and } 135°\}$, the contrast is calculated as $$CON_\emptyset = \Sigma_i \Sigma_j P(i,j)(i-j)^2 \quad (11)$$

b) Fractal Dimension

Objects that have integer dimensions conform to traditional Euclidean geometry. Those objects that possess the property of self-similarity are known as fractals. The fractal dimension of a subset of fractals, known as wild fractals is calculated using a box count method.

The image $I(n_1, n_2)$ is put onto a grid with mesh size s. The number of grid boxes that contain a portion of the structure is described by the power law $$B(s) = \frac{1}{s^D} \quad (12)$$

where D is the fractal dimension and is given as $$D = \frac{\log_{10} B(s)}{\log_{10}\left(\frac{1}{s}\right)} \quad (13)$$

Figure 6:
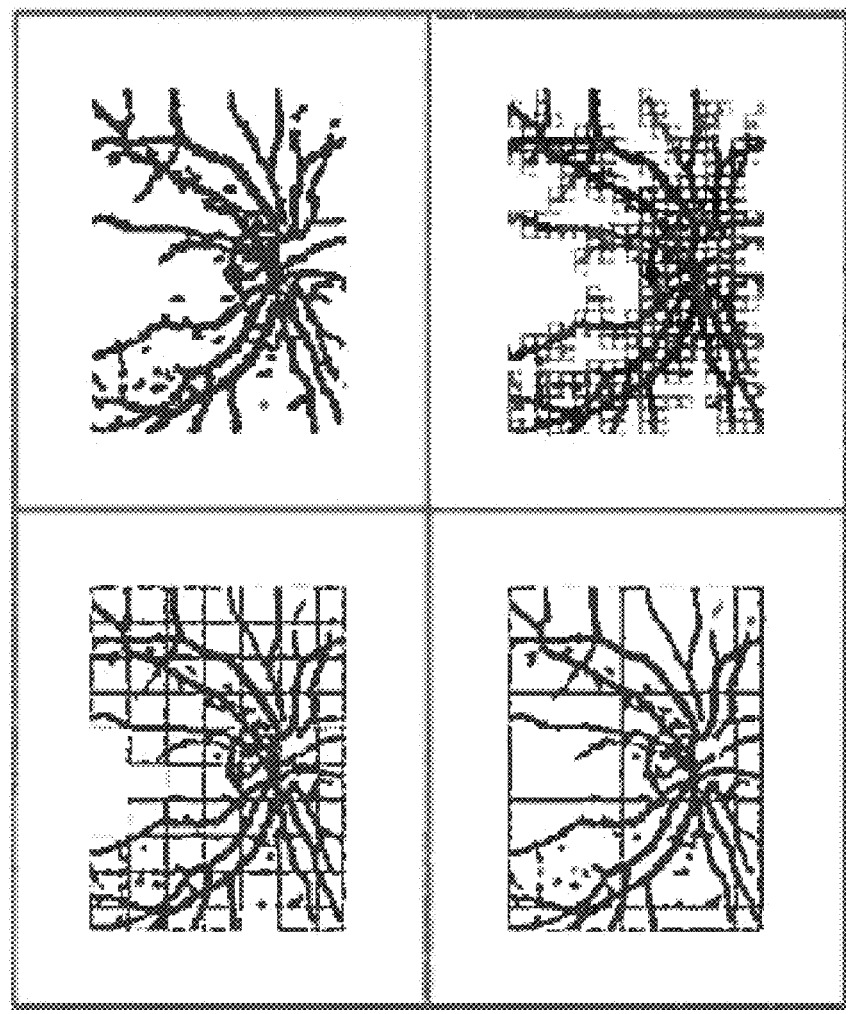
FIG. 6. Diagrammatic representation of box count method.

The box count algorithm for a blood vessel edge profile map is pictorially represented in FIG. 6.

c) Lacunarity

Lacunarity provides the distribution of gaps or holes in an image. It is considered as textural representation of a fractal. The idea is to map the image It: $[N_1, N_2] \to R$ onto a surface S in the following way $$S = \{i, j, f(i,j)/(i,j) \in [1:N_1] \times [1:N_2]\} \quad (14)$$

where $f(i,j) = \{(1,2, \ldots, I_{tmax}) | f = I_t(i,j)\}$, with $I_{tmax}$ being the maximum gray level intensity present in the image. The probability distribution function can be expressed as $$Q(s, r) = \frac{b(s, r)}{B(r)} \quad (15)$$

b(s, r) is the number of boxes with side r containing s points of the surface representing the object whose lacunarity must be established and B(r) is the total number of boxes with side r. The first and second moments are calculated as $$Z_1(r) = \Sigma_{s=1}^{s_{max}} s \times Q(s,t) \quad (16)$$

$$Z_2(r) = \Sigma_{s=1}^{s_{max}} s^2 \times Q(s,r) \quad (17)$$

The ratio of the moments defined in eqns. 16 and 17 is formulated as $$\Lambda(T) = \frac{z_1(r)}{z_2(r)} \quad (18)$$

Lacunarity is defined by $$\lambda = \frac{d\Lambda(r)}{dr} \quad (19)$$

Figure 7:
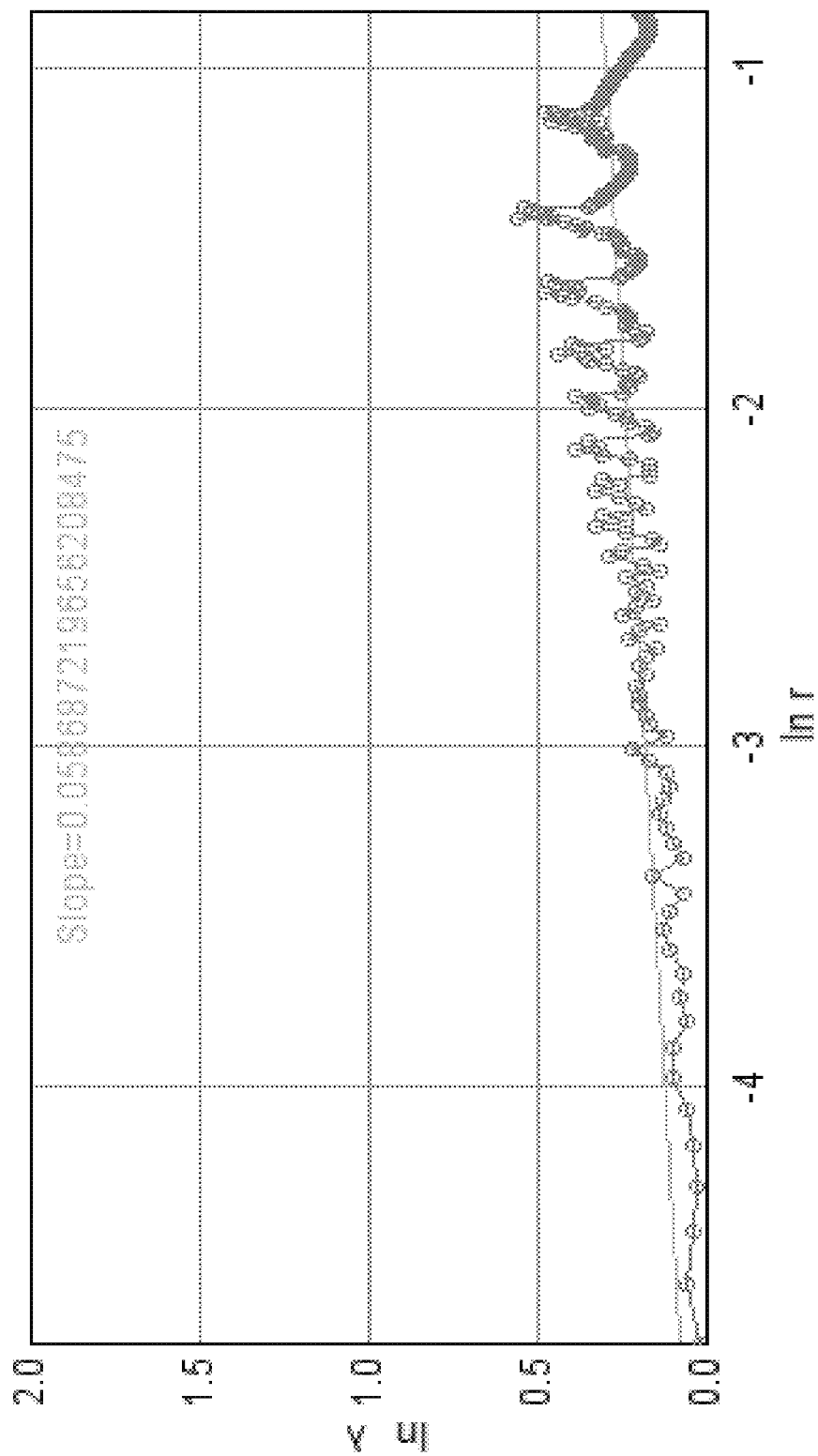
FIG. 7. Lacunarity considering foreground pixels versus box size, r.

The lacunarity is calculated for foreground pixels as well as for foreground pixels plus background pixels. FIG. 7 shows a plot of lacunarity versus box size on a logarithmic Classification A classifier such as neural network or support vector machines (SVM) that is linear or has piecewise linear approximation capabilities with known implementation is particularly attractive since it provides an efficient means of hardware realization. In this case, ANN as well as SVM is utilized for classification.

A three layer, feed-forward artificial neural network is used to implement classification using a backpropagation training algorithm. The first layer is the input layer and the number of neurons depends on the number of features. The second layer is the hidden layer and the number of neurons in this layer is determined empirically. The output layer consists of three neurons, each pertaining to a class—normal, NPDR and PDR.

SVM is a classification technique that provides a useful perspective from another paradigm. As described herein, a multiclass, one-against-one training is employed to provide the best hyperplane for separation of the three classes. The main objective is to minimize the function $$f(w,b,\xi)=\tfrac{1}{2}w^T\cdot w+C\Sigma_i\xi_j \qquad (20)$$

subject to the condition $$y(w^T\times x_i+b)\geq 1-\xi_i, \xi_j\geq 0 (\text{for all } x_i) \qquad (21)$$

where $x_i$, i=1, 2, 3, . . . , N is the feature vector, w is the weight vector, C is a penalty parameter that compensates for misclassification and ξi are known as slack variables. The quadratic optimization technique involves solving Lagarangian multipliers and Karush-Kuhn-Tucker (KKT) conditions. The output, defined by the three classes: Normal, NPDR and PDR is given as $$y=\Sigma_{i=1}^{nsv}(\alpha_i,\alpha_i^a)K(x,x_i)+b \qquad (22)$$

where $\alpha_i$, $\alpha_i^a$, i=1, 2, . . . , N are Lagarangian multipliers, K(x, xi) the inner product kernel that satisfies Mercer's condition and nsv refers to the data corresponding to non-zero $\alpha_i$, $\alpha_i^a$ pairs.

In this work, the entire dataset was divided into training and testing sets using a two-fold cross-validation by varying the holdout parameter from 0.1 to 0.9 in steps of 0.1. The results reported is the average classification accuracy.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Figure 8:
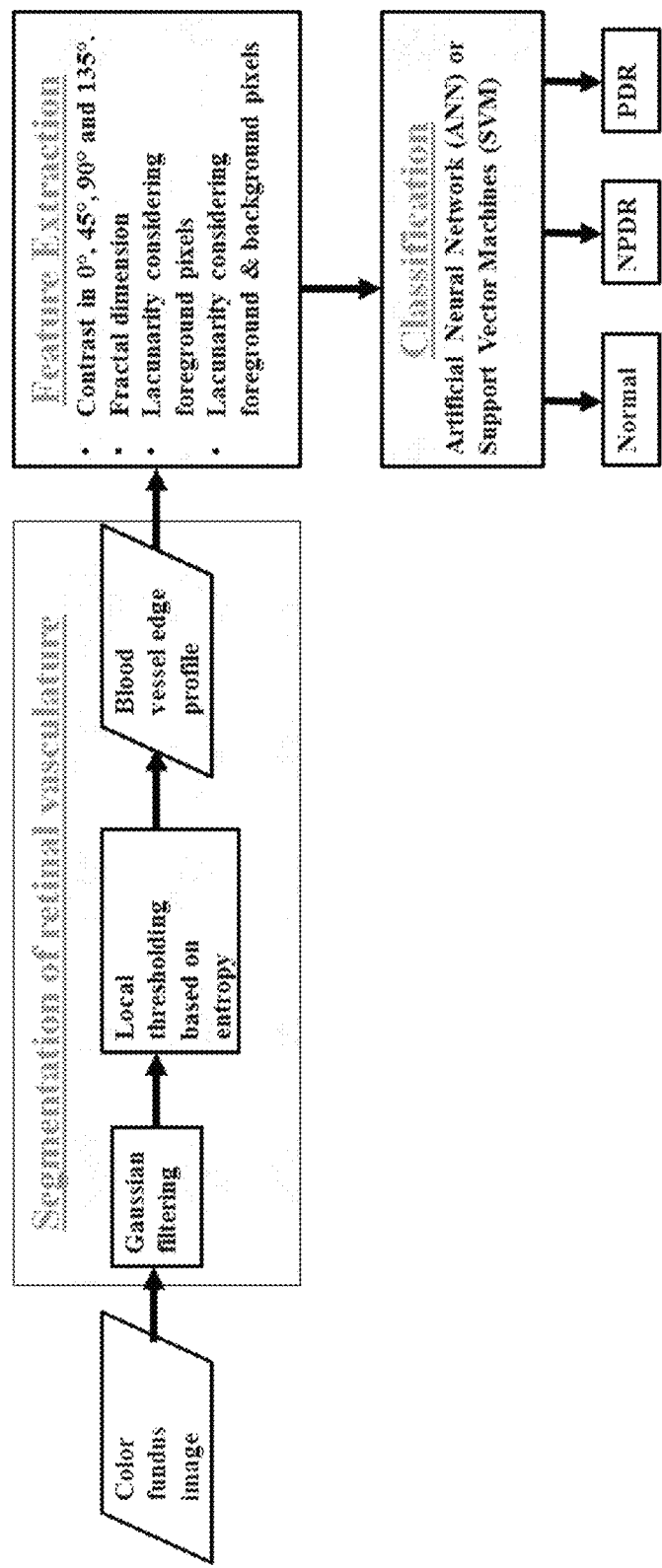
FIG. 8. Detailed block diagram of Example 1.

This Example was conducted on a set of 69 images. There were 19 images belonging to the Normal class, 33 NPDR images and 17 images from the PDR class. A detailed block diagram depicting various stages in Example 1 is as shown in FIG. 8.

Figure 9:
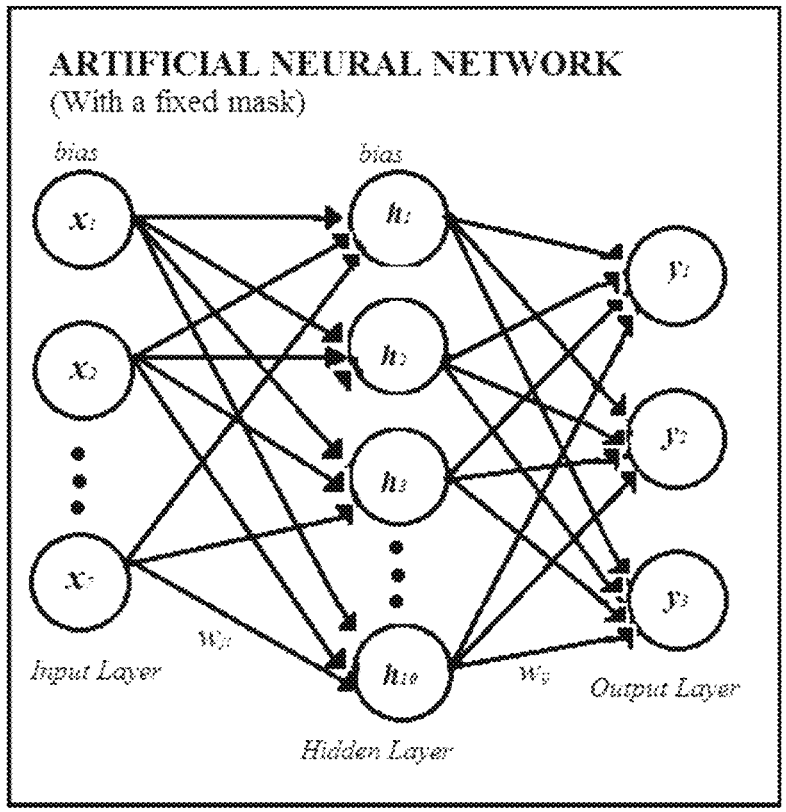
FIG. 9. Schematic diagram of ANN for Example 1.
Figure 10:
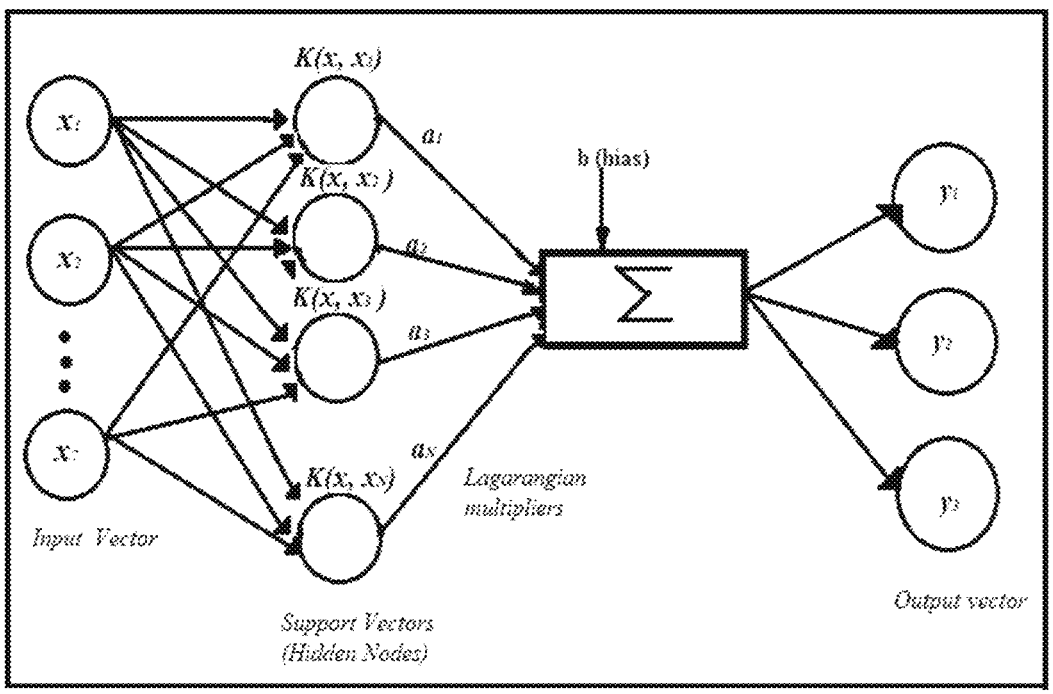
FIG. 10. Schematic diagram of SYM for Example 1.

The Example follows the steps outlined herein. The blood vessel edge profile is generated using a fixed mask prior to thresholding. This denotes that a single value of standard deviation is used for every input image in the Gaussian kernel function given in eqn. 4. The following step involved extracting all the seven features as described herein Classification using the ANN involved seven neurons in the input layer. The outline of ANN for this Example is indicated in FIG. 9. FIG. 10 illustrates the outline of the SVIV structure analogous to the neural net.

This example has a number of control parameters or variables out of which the edge detection modelling number of samples and feature space has been deemed the most crucial based on the outcome of Example 1.

Results for Example 1

Figure 15A:
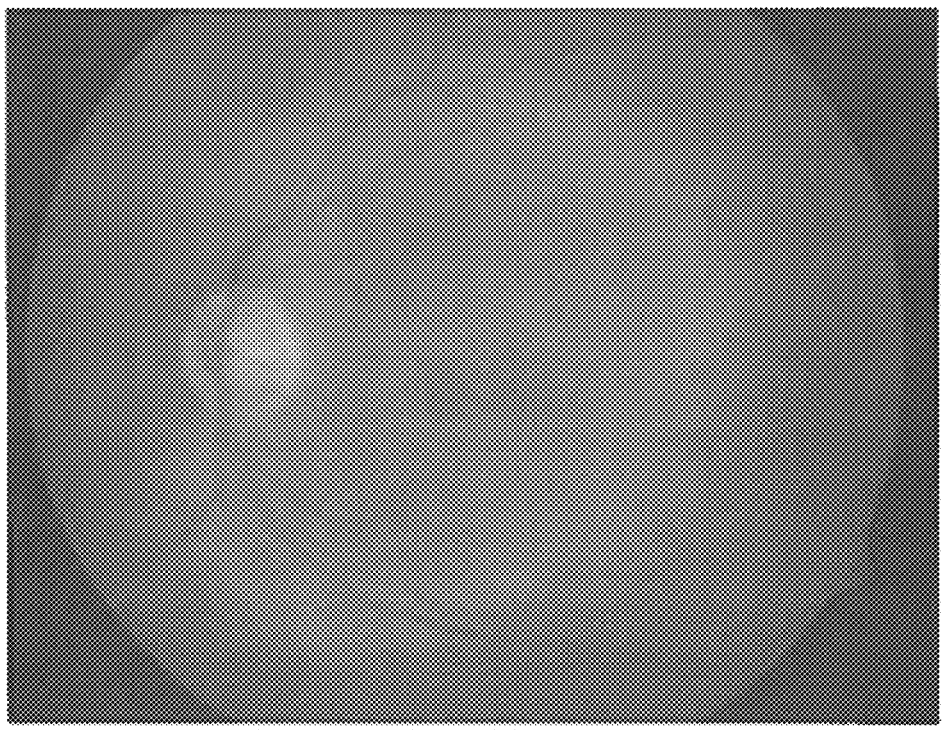
FIG. 15A. Original color fundus image for class normal.
Figure 15B:
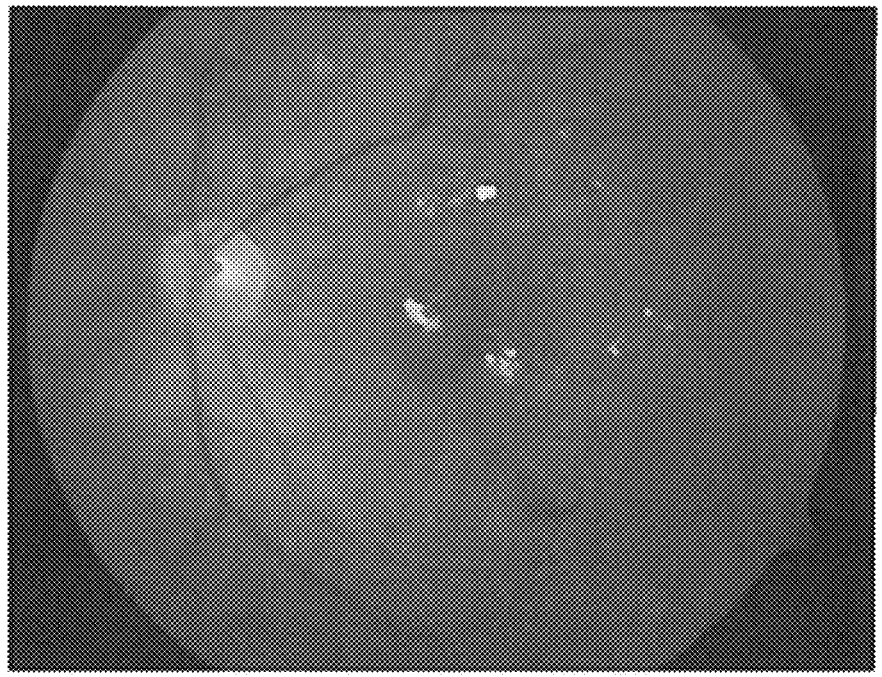
FIG. 15B. Input color fundus image from Non-Proliferative Diabetic Retinopathy (NPDR) class.
Figure 15C:
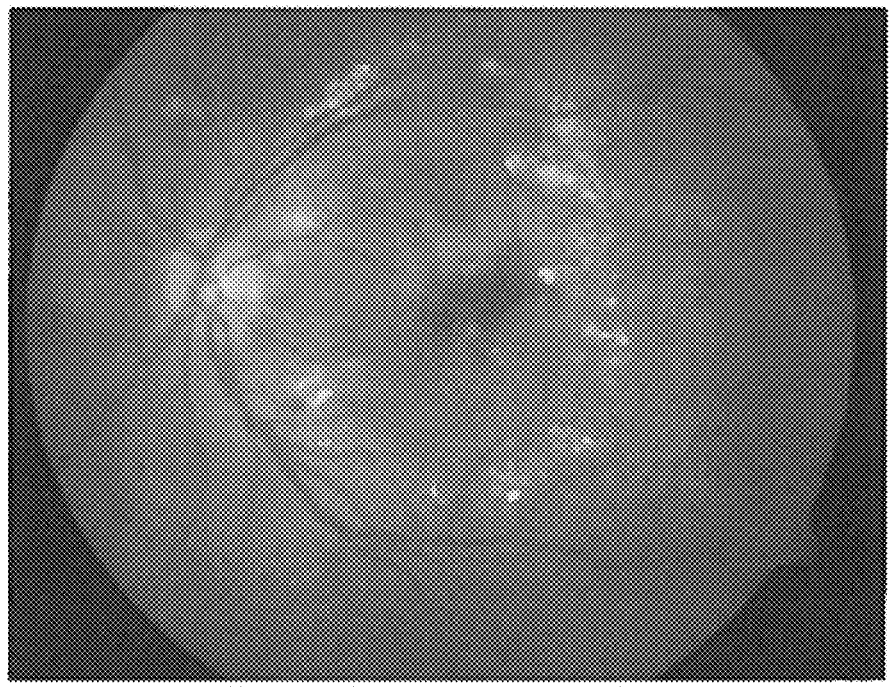
FIG. 15C. Retinal input image from the Proliferative Diabetic Retinopathy (PDR) class.

The original color fundus images from the DIARETDBI database were of size 1500×1152 and those from the DRIVE database were of size 565×584. FIGS. 15A, 15B and 15C illustrate the original images from Normal, NPDR and PDR classes.

The segmentation of retinal vasculature yields a blood vessel edge profile map which is essential to isolate the healthy blood vessels and various disease anomalies. This map overlaid on the original images has been depicted in FIG. 1 for all the three classes.

Figure 17:
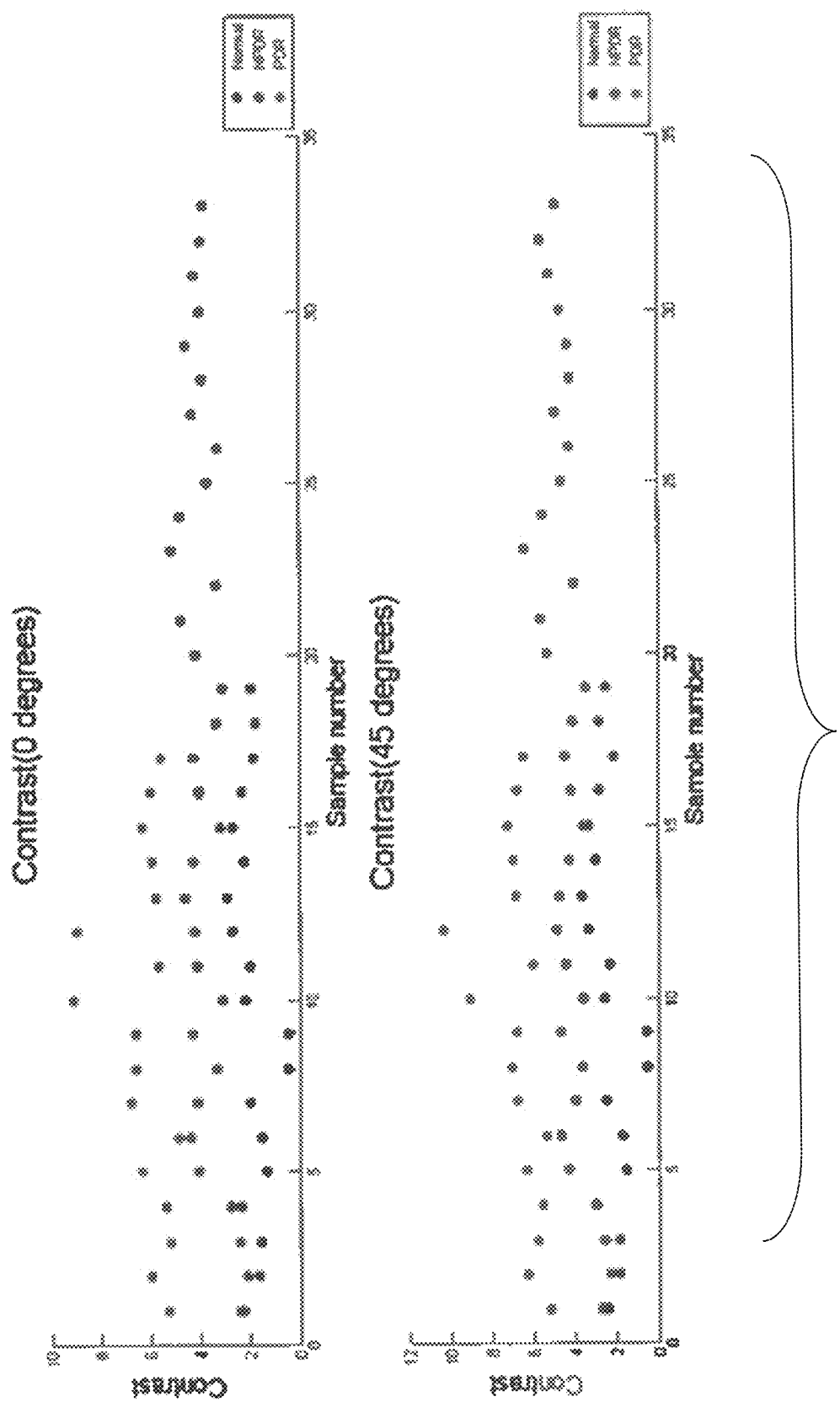
FIG. 17. GLCM based contrast in 0° and 45° orientations.
Figure 18:
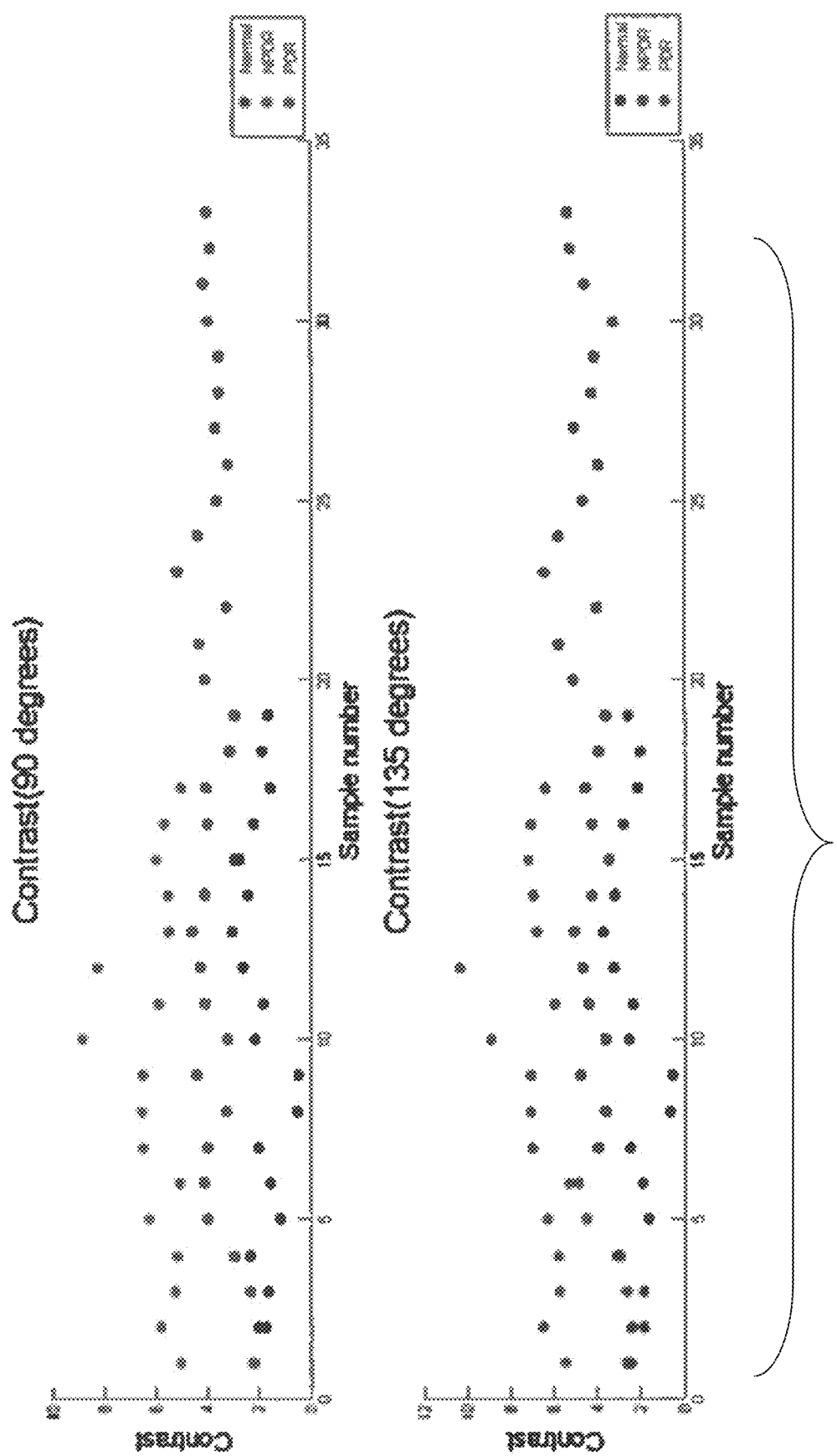
FIG. 18. Textural contrast in 90° and 135° orientations.
Figure 19:
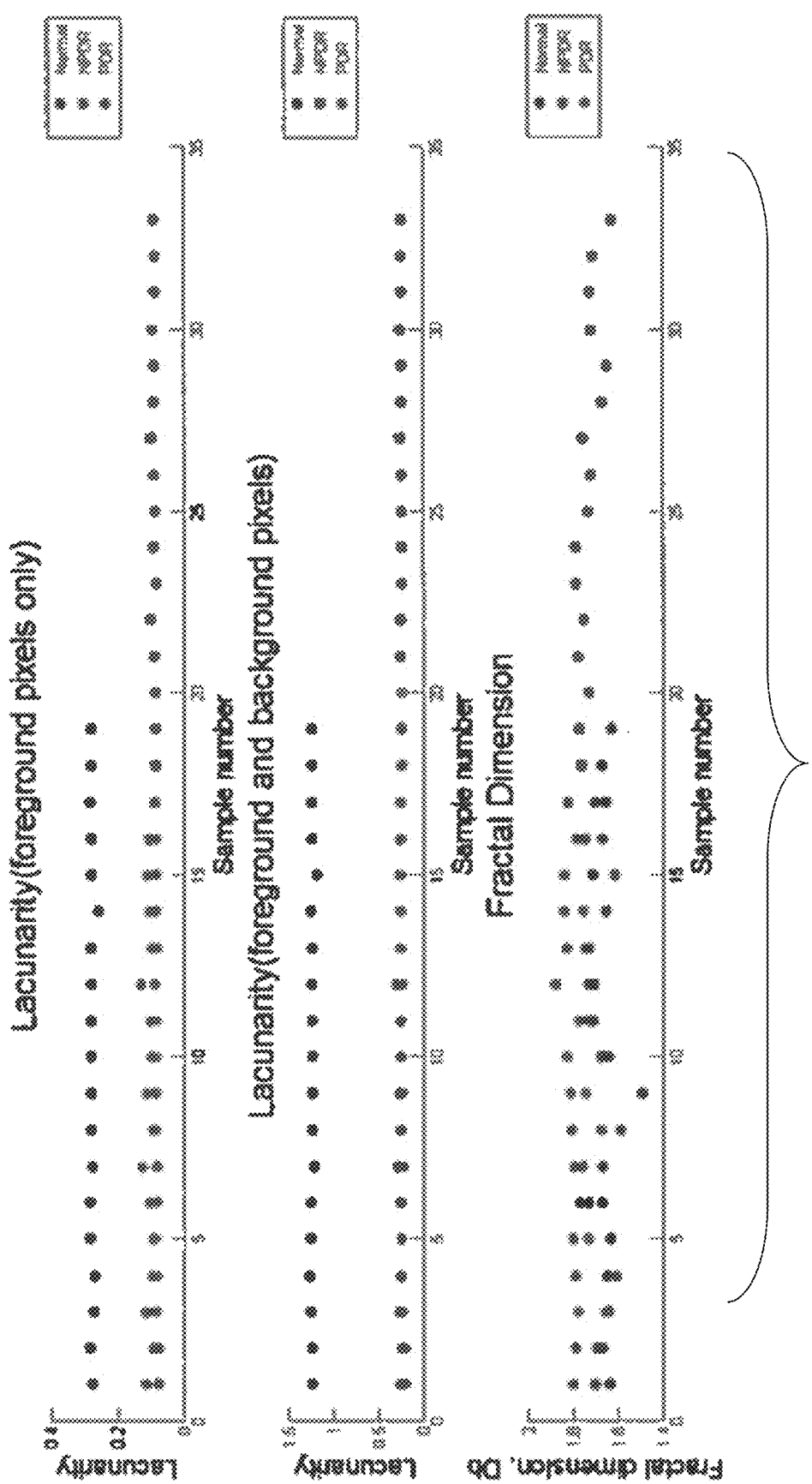
FIG. 19. Scatter plot of the fractal features.
Figure 20:
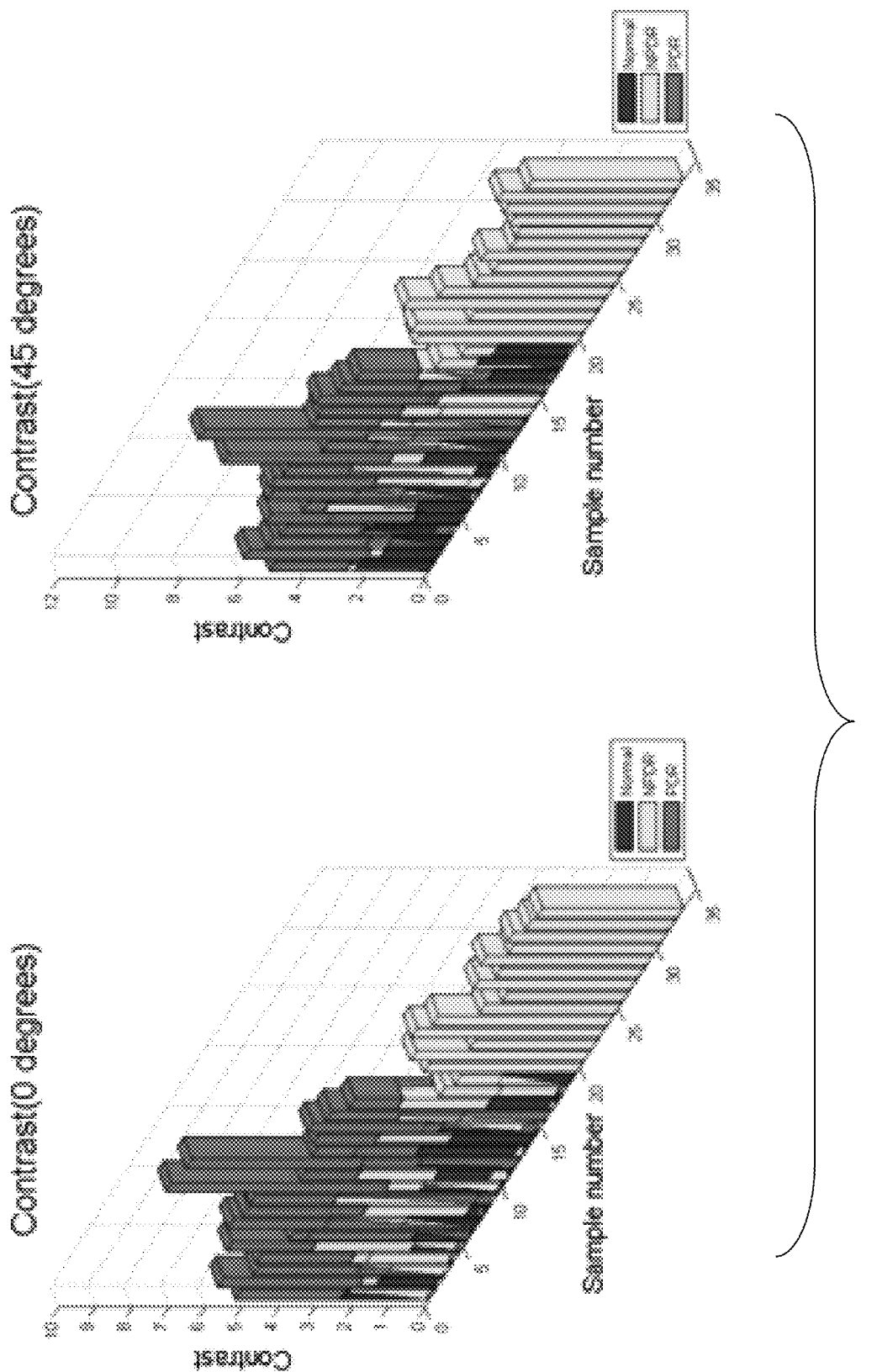
FIG. 20. Bar graph representation of GLCM based contrast in 0° and 45°.
Figure 21:
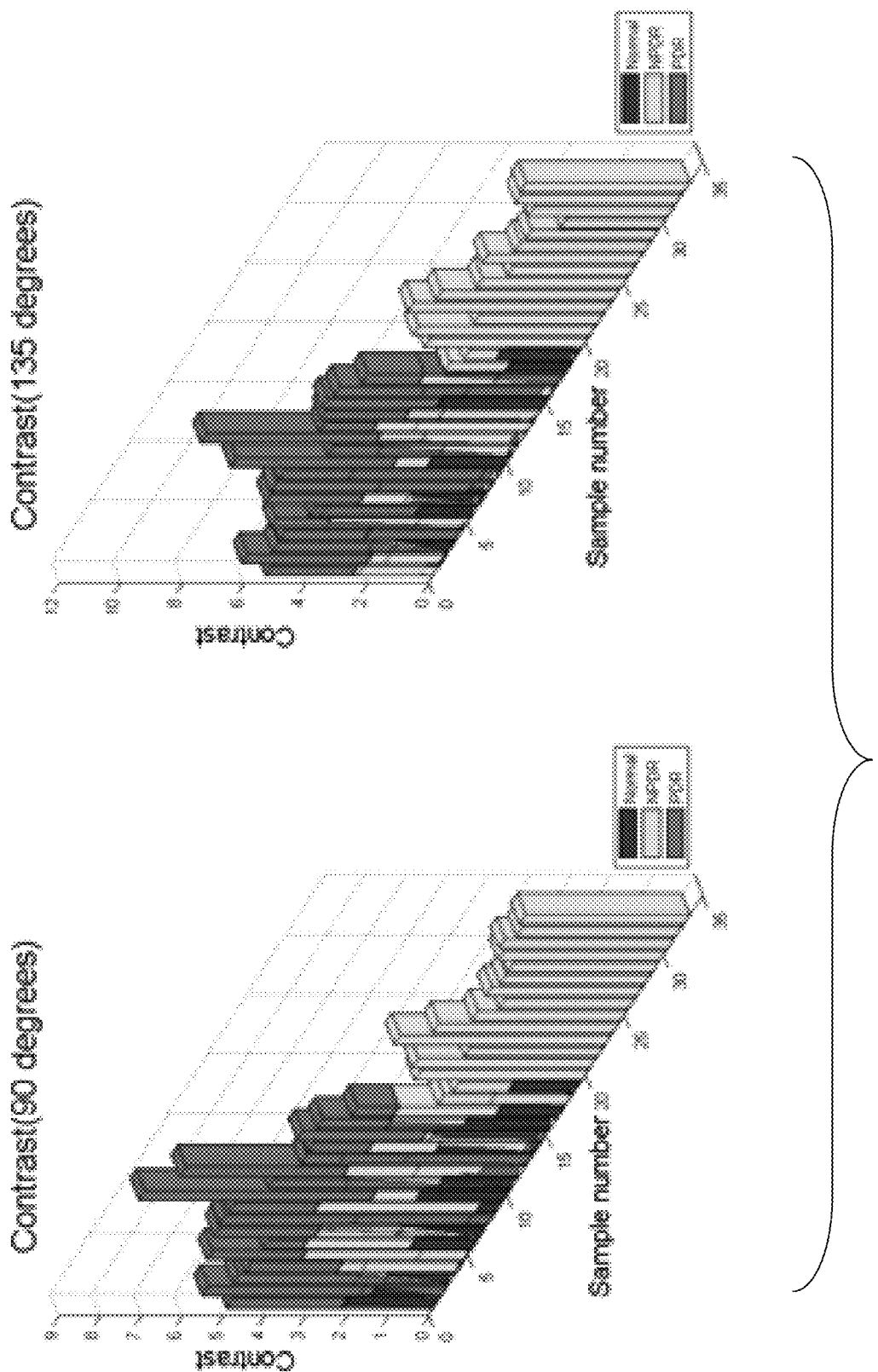
FIG. 21. Haralick's co-occurrence matrix based contrast in 90° and 135°.
Figure 22:
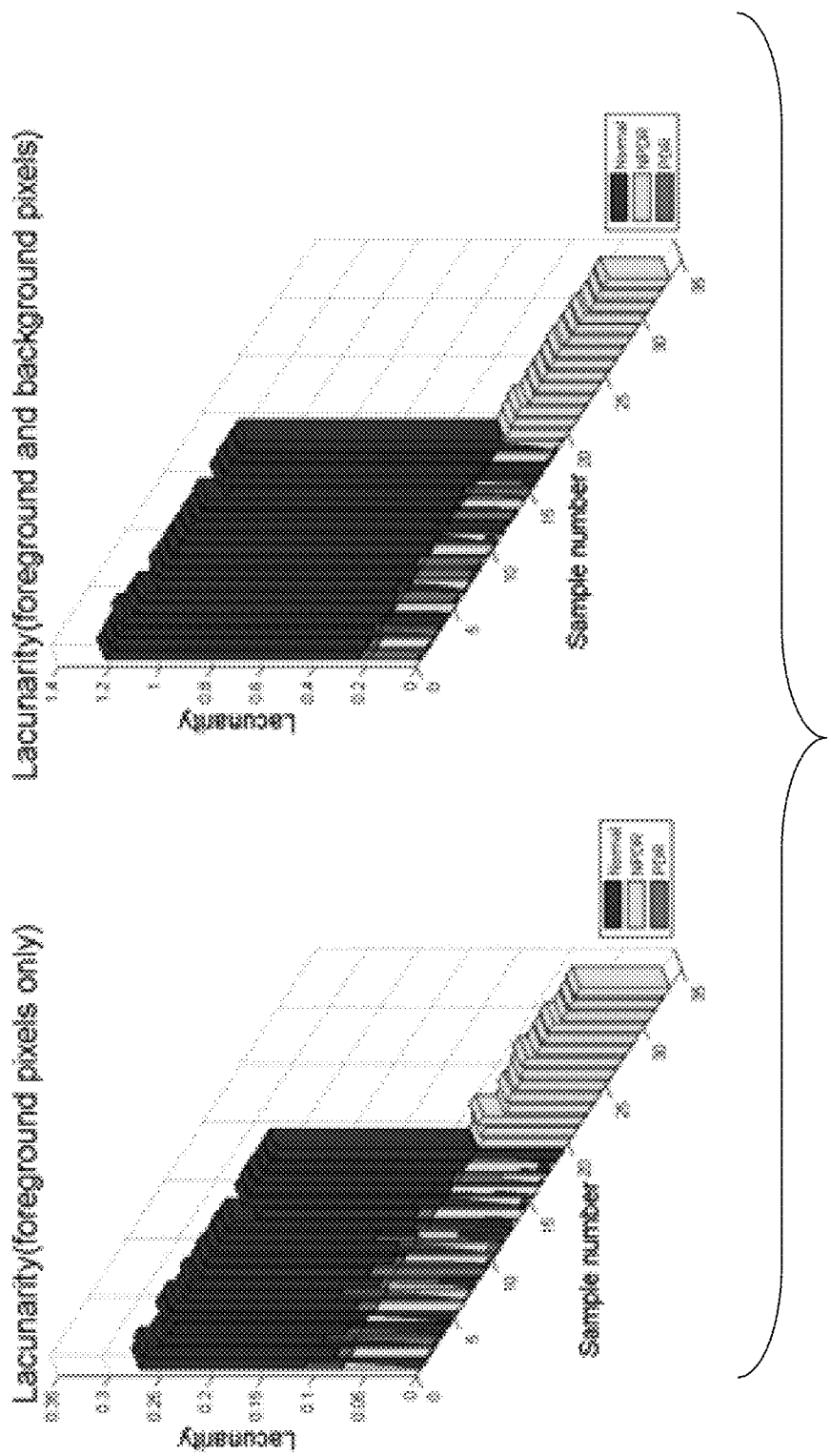
FIG. 22. Bar graph plots of Lacunarity.
Figure 23:
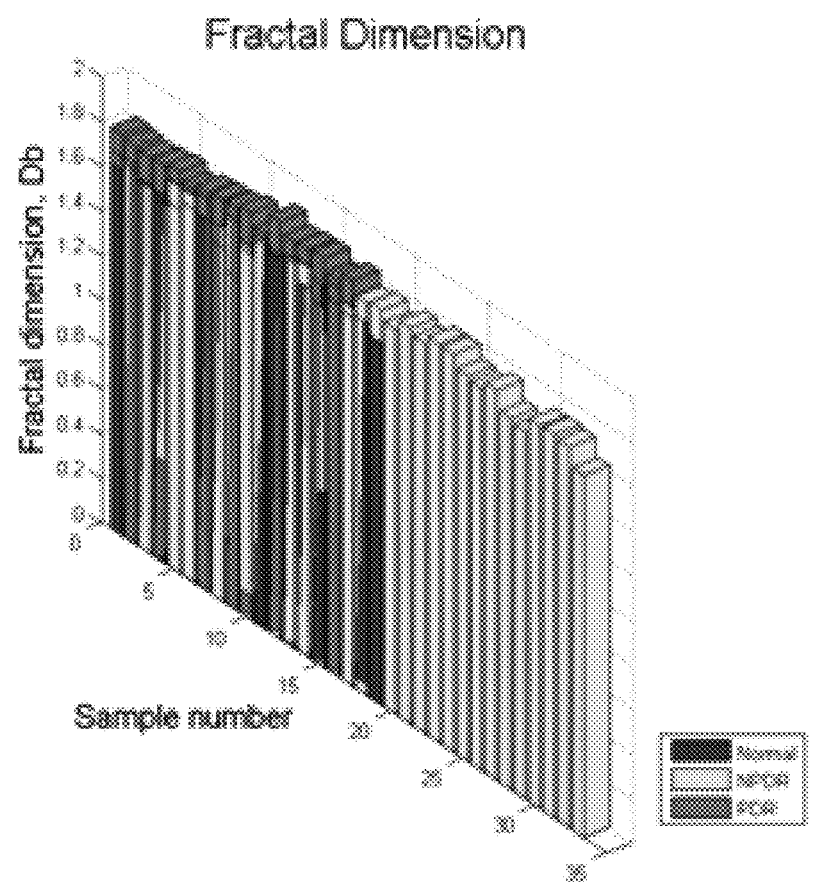
FIG. 23. Bar graph representation of fractal dimension.
Figure 24A:
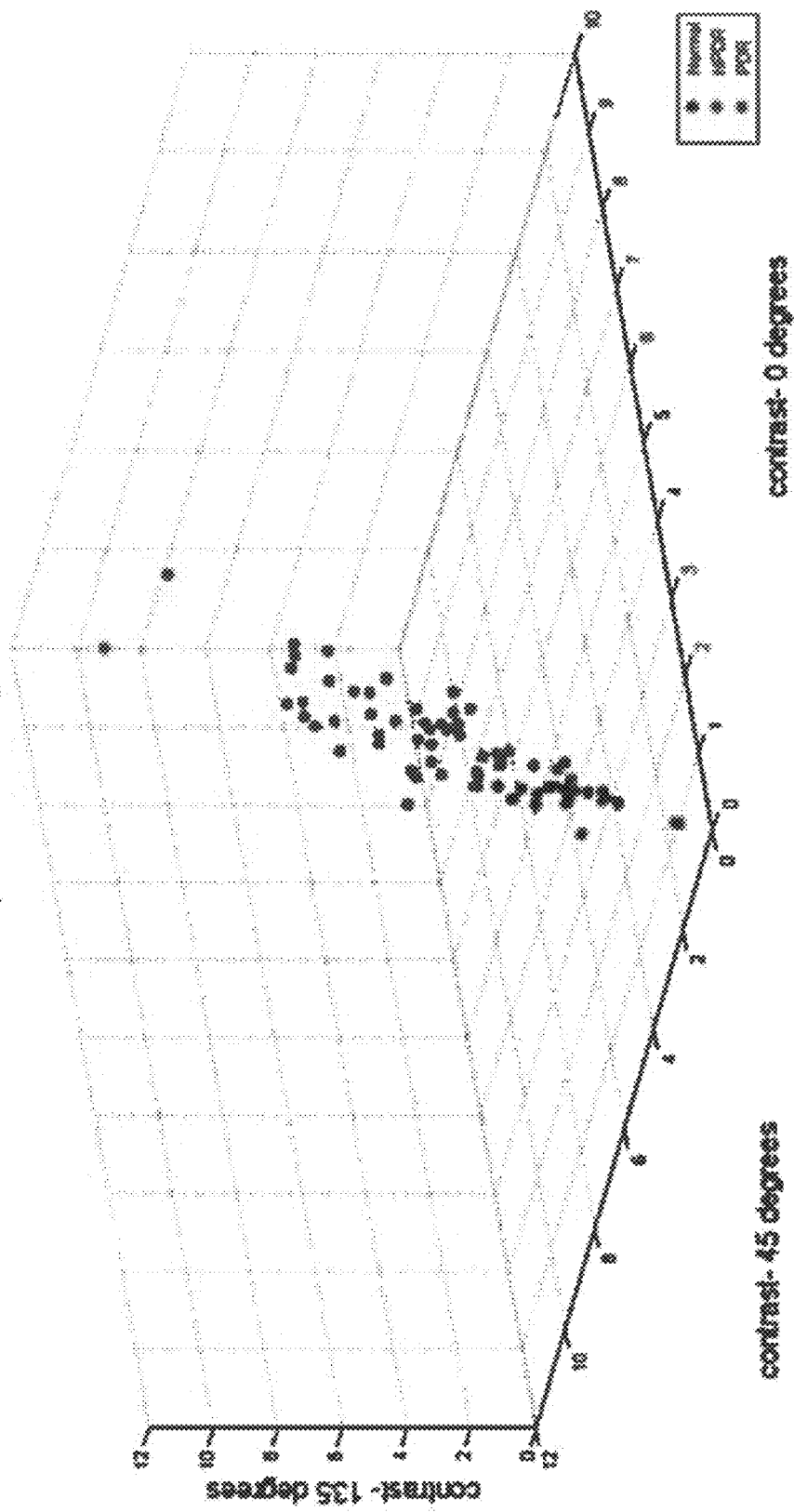
FIG. 24A. Contrast in 0°, 45° and 135°.
Figure 24B:
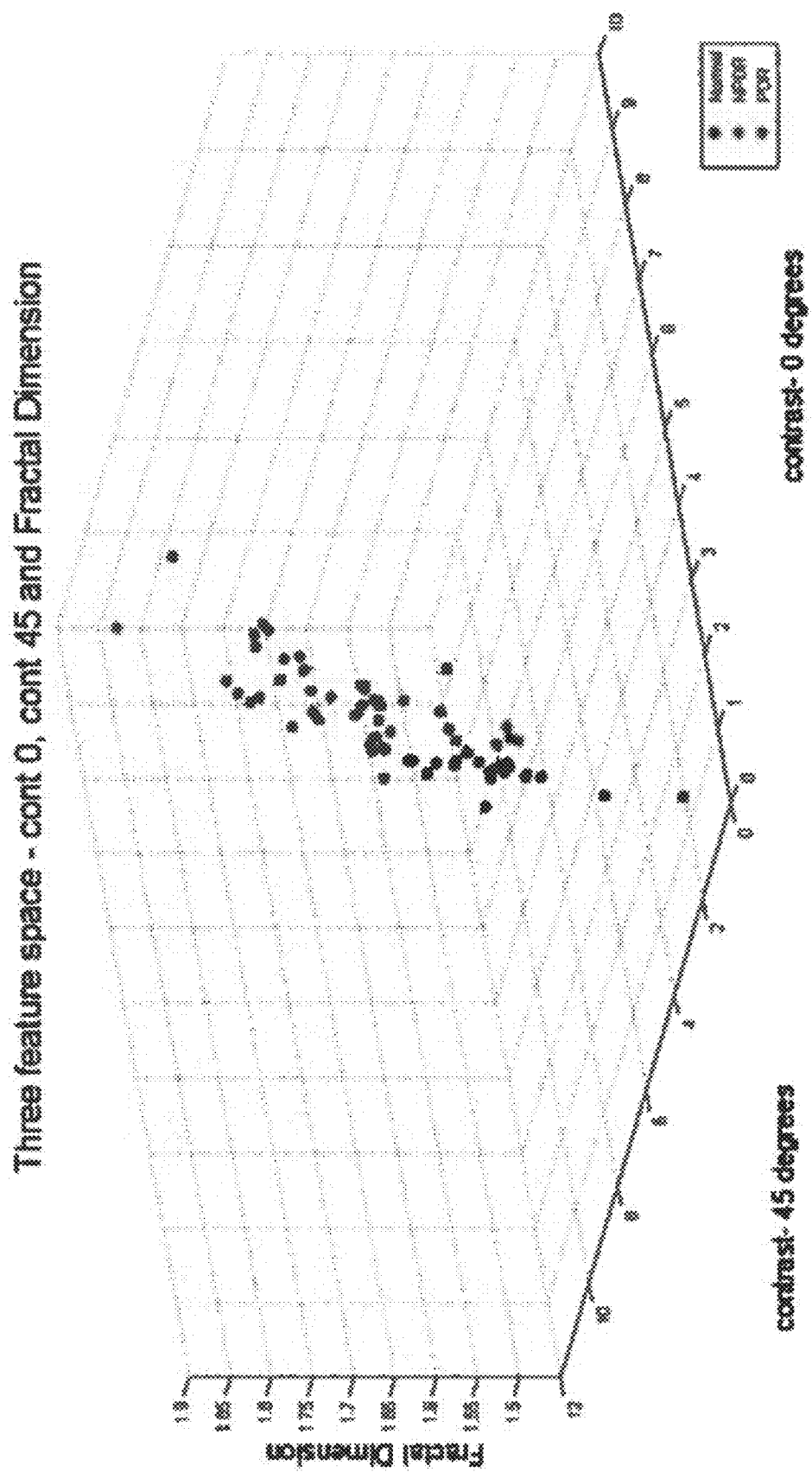
FIG. 24B. Contrast in 0°, contrast in 45° and fractal dimension.
Figure 24C:
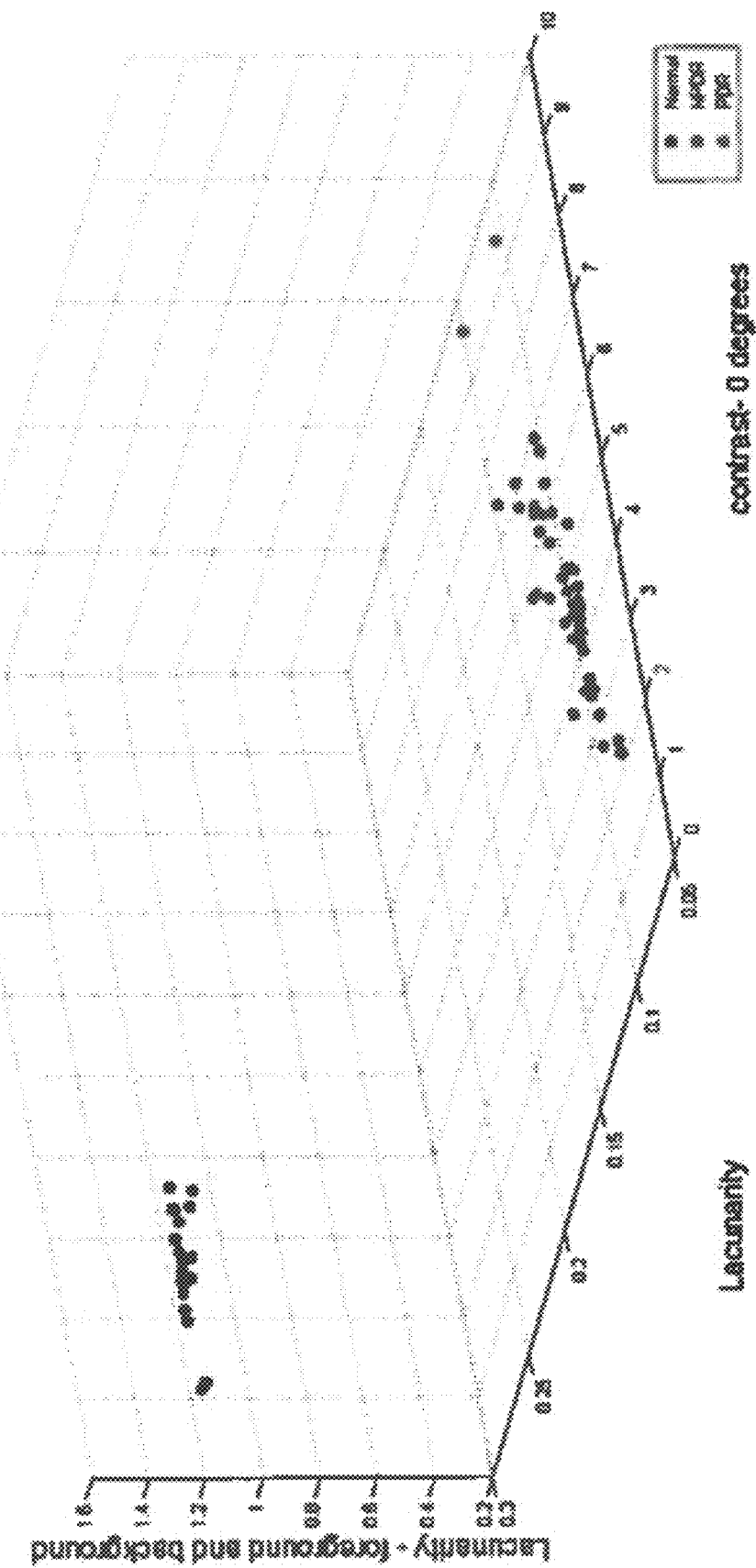
FIG. 24C. Contrast in 0°, lacunarity considering foreground pixels and lacunarity considering foreground pixels and empty spaces.
Figure 24D:
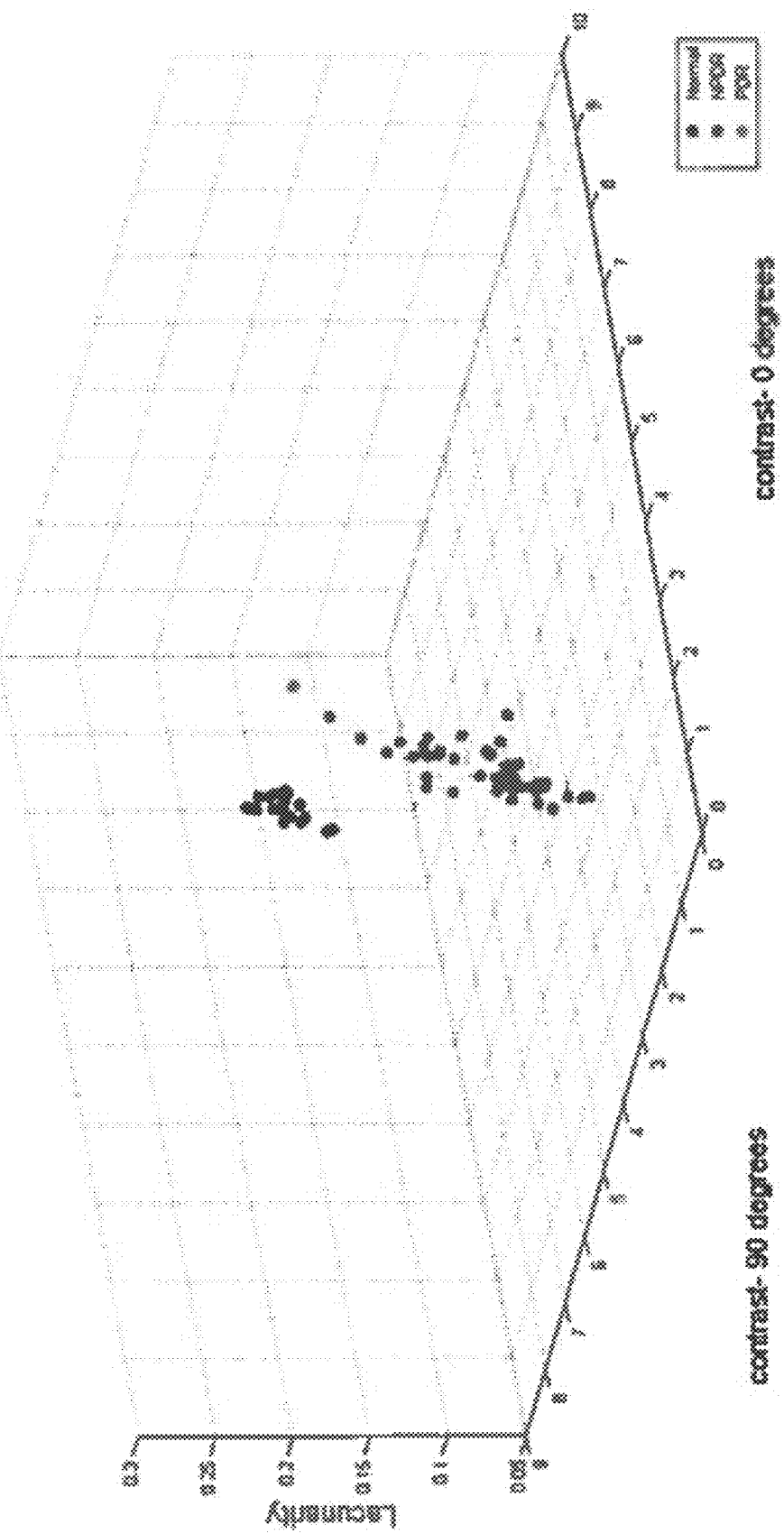
FIG. 24D. Contrast in 0°, 90° and lacunarity considering foreground pixels.

Based on the flowchart illustrated in FIG. 1, the attributes that are unique to each class are described. The seven features extracted in this Example provide a unique description about the individual classes. The spatial inter-relationship between the pixels is provided by the contrast in four directions. The fractal features uniquely characterize the presence of anomalies. The scatter plots for all the features are shown in FIG. 17 through FIG. 19.

The seven individual features have been represented in two dimensional bar graphs, as indicated in FIG. 20 through FIG. 23.

It can be seen from the scatter as well as the bar graph plots that the NPDR class has characteristics that are similar to the other two classes. In the plots shown in FIGS. 20-23, the NPDR class has between the normal and PDR classes and hence it is the most difficult to classify. The results of classification using ANN and SMV arc indicated below in Table 2.

TABLE 2

| Classification accuracy and sensitivity | | |
|---|---|---|
| Type of classifier | Classification accuracy (%) | Sensitivity (%) |
| ANN | 91.7 | 93 |
| SVM | 93.0 | 97 |

The seven dimensional feature space was represented as a subset of three dimensional spaces. As a result of which 35 plots were generated. The plots with features only from texture features and plots containing only fractal features are shown along with plots that contain a combination of the above in FIGS. 24A-24D.

It can be seen that a combination of contrast in 0°, contrast in 90° and lacunarity considering foreground pixels only provide a good separation between the three classes.

Example 2

In this Example, the sample set from Example 1 was increased to 106 images from the same databases.

A general adaptive image processing system involves the use of information from the input image along with apriori information in order to produce a more reliable output.

The adaptive mask generation procedure to segment the retinal vasculature was utilized as an improvement of fixed mask approach in Example 1. The number of samples was increased from 69 to 106. The seven dimensional feature space was represented as a subset of three dimensional feature spaces. A simple block diagram illustrating the concept is shown in FIG. 11.

The system impulse response $h(n_1, n_2)$ is input driven and it is defined by the Gaussian kernel.

$$h(n_1, n_2) = G(n_1, n_2) = \frac{1}{2\pi\sigma^2} e^{\frac{-n_1^2}{2\sigma^2}}, |n_2| \leq \frac{L}{2} \quad (23)$$

where σ and L have been defined as in eqn. 4.

This implies that the standard deviation utilized in the kernel function is based on the input fundus image. The mask generated is a linear convolution between the system impulse response and the input grayscale image. It is given as $$M(n_1,n_2) = h(n_1,n_2) * I(n_1,n_2) \quad (24)$$

Figure 12:
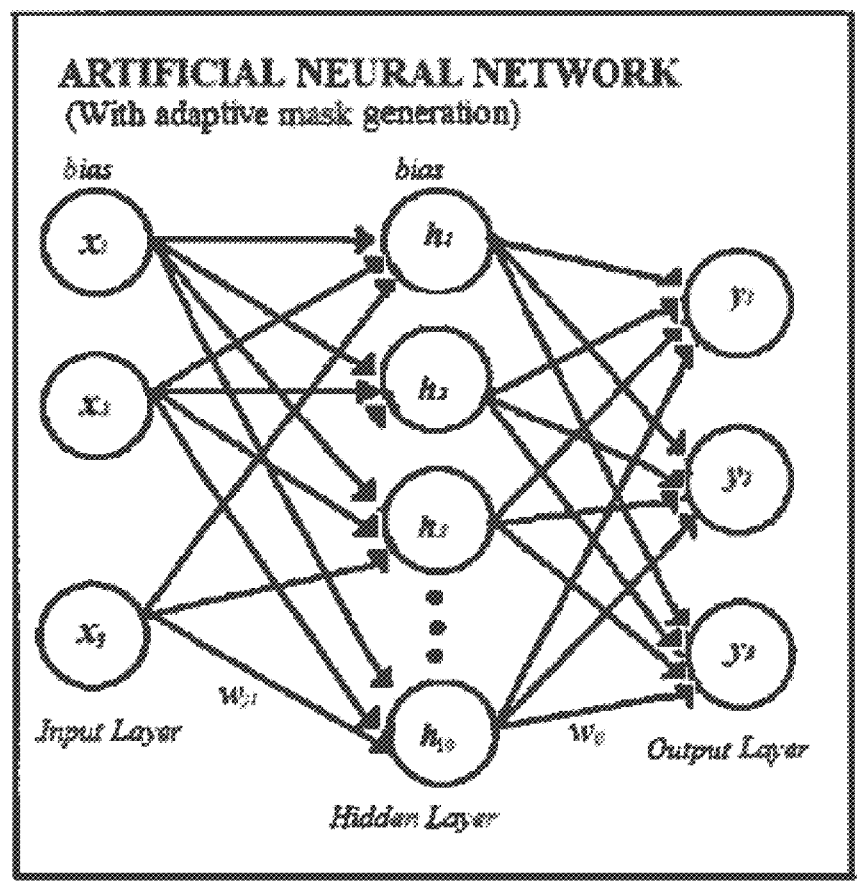
FIG. 12. Structural representation of ANN for Example 2.
Figure 13:
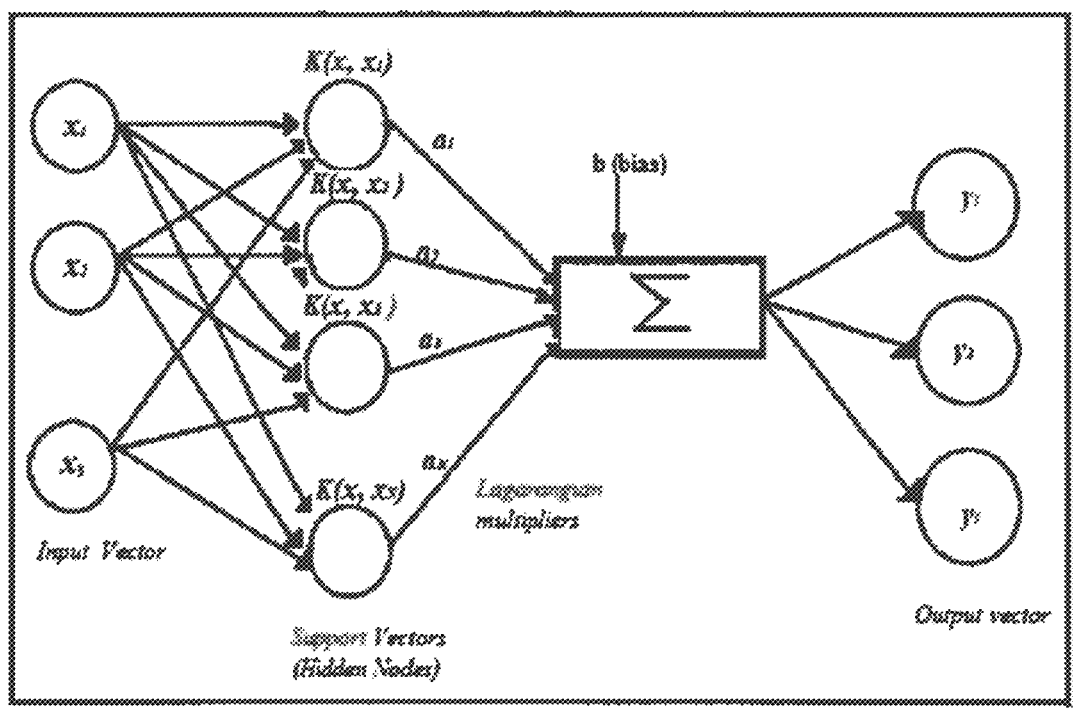
FIG. 13. Framework of SVM classifier for Example 2.
Figure 14:
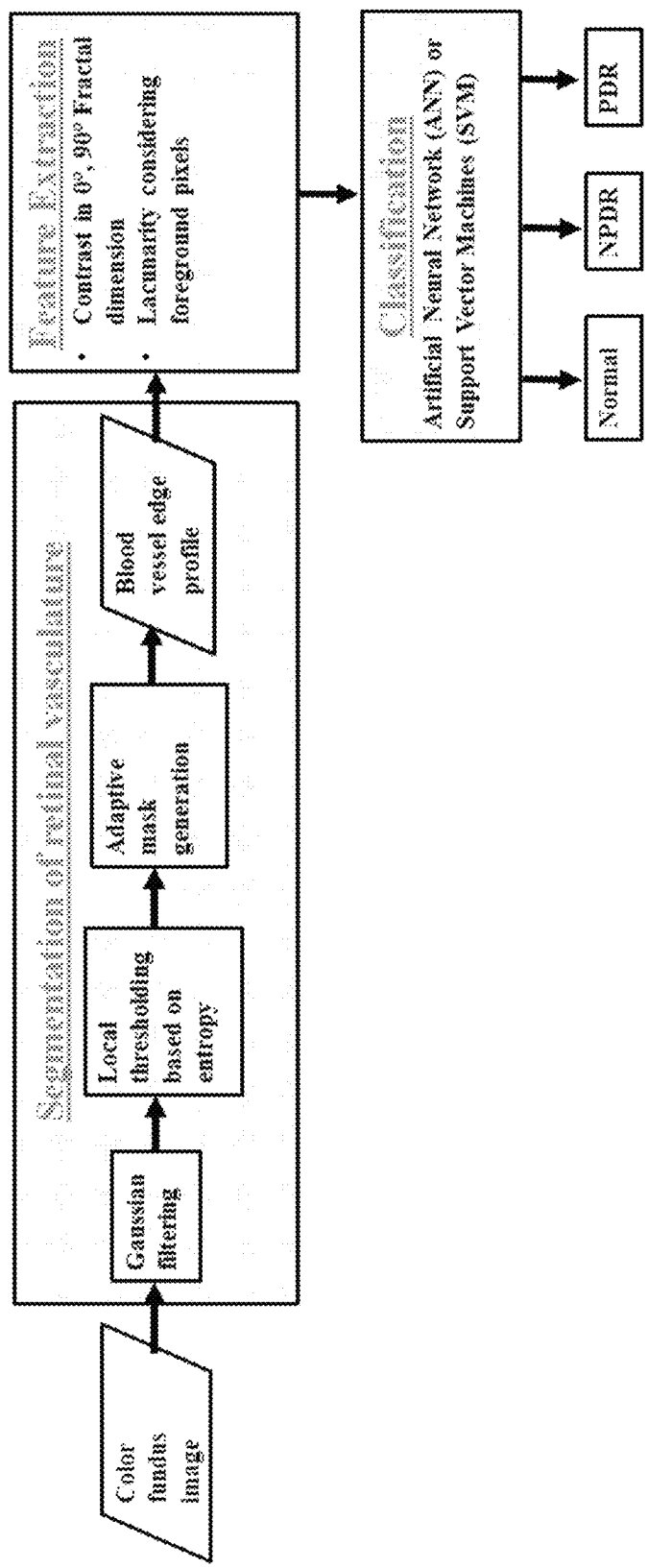
FIG. 14. Detailed block diagram for Example 2.

The remaining steps in the procedure to segment the retinal vasculature is as described by eqn. 6 through eqn. 10. During the feature extraction phase, three features, namely, contrast in 0° and 90° and lacunarity considering foreground pixels only are utilized. The outline of the classifiers for this Example is illustrated in FIG. 12 and FIG. 13. A block diagram explaining the various steps for Example 2 is shown in FIG. 14.

Results of Example 2

The Example was conducted on a sample size of 106 images. The adaptive mask generation procedure improved the detection of the blood vessels and anomalies in the color fundus image. FIGS. 265-265 illustrates the blood vessel edge profile map overlaid on the original color fundus images for normal, NPDR and PDR classes, respectively.

Figure 16A:
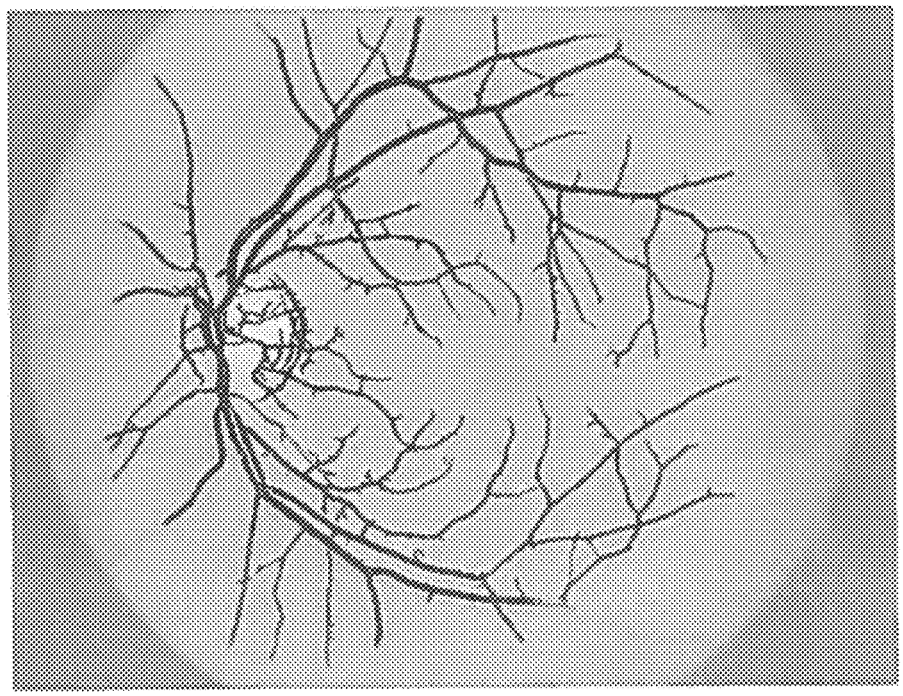
FIG. 16A. Blood vessel edge profile map of a healthy retina.
Figure 16B:
FIG. 16B. Blood vessel edge profile of a retina from NPDR class.
Figure 16C:
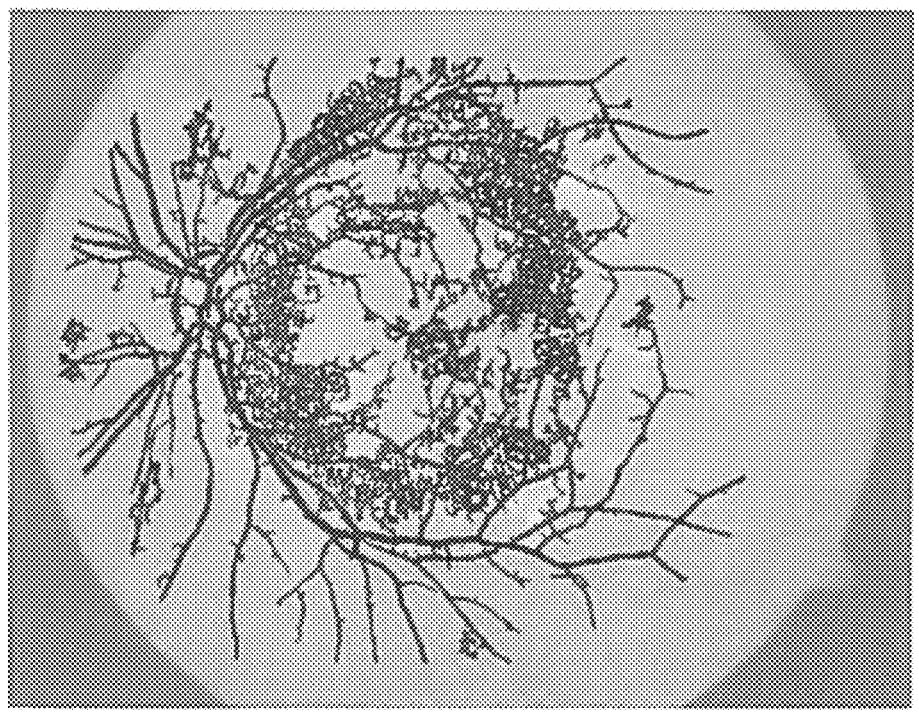
FIG. 16C. Retinal blood vessel edge profile map of a patient diagnosed with PDR.
Figure 25A:
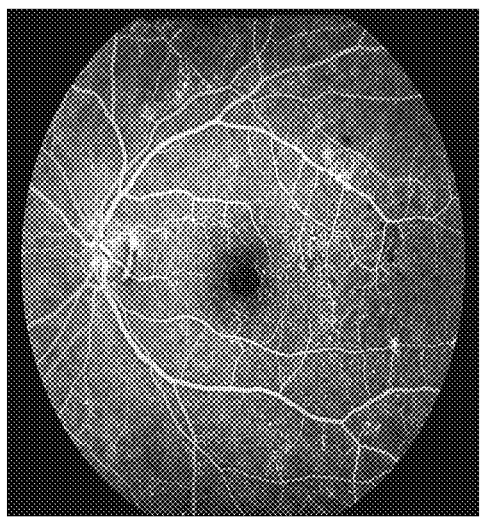
FIG. 25A. Blood vessel edge profile map of a healthy retina.
Figure 25B:
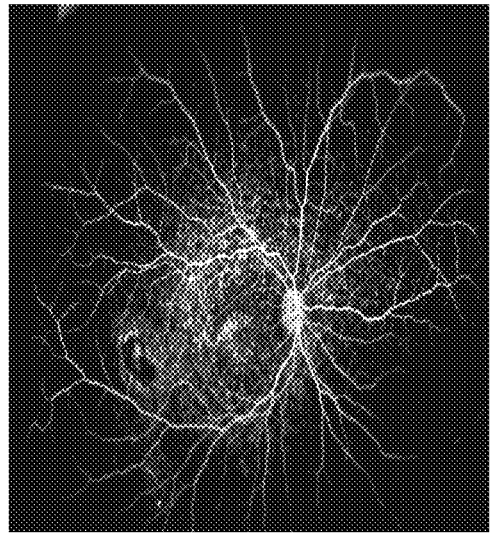
FIG. 25B. Blood vessel edge profile of a retina from NPDR class.
Figure 25C:
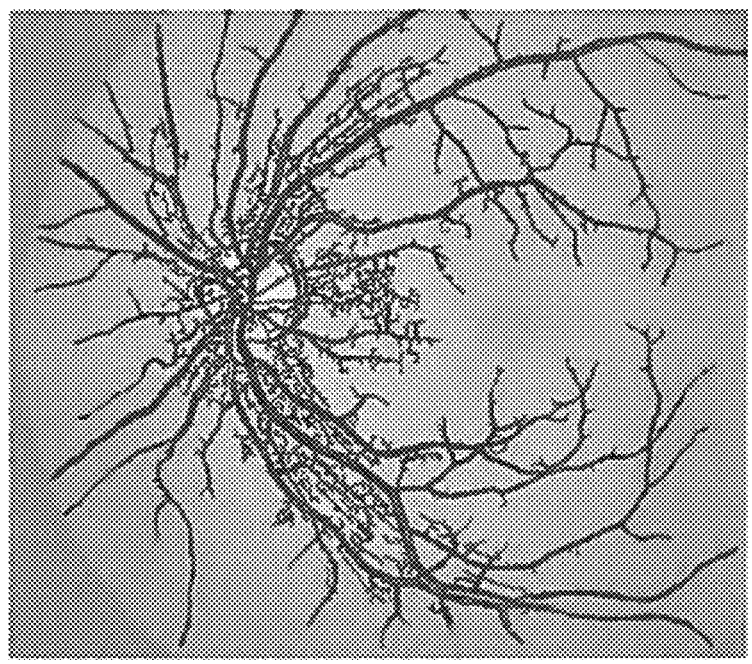
FIG. 25C. Retinal blood vessel edge profile map of a patient diagnosed with PDR.
Figure 26A:
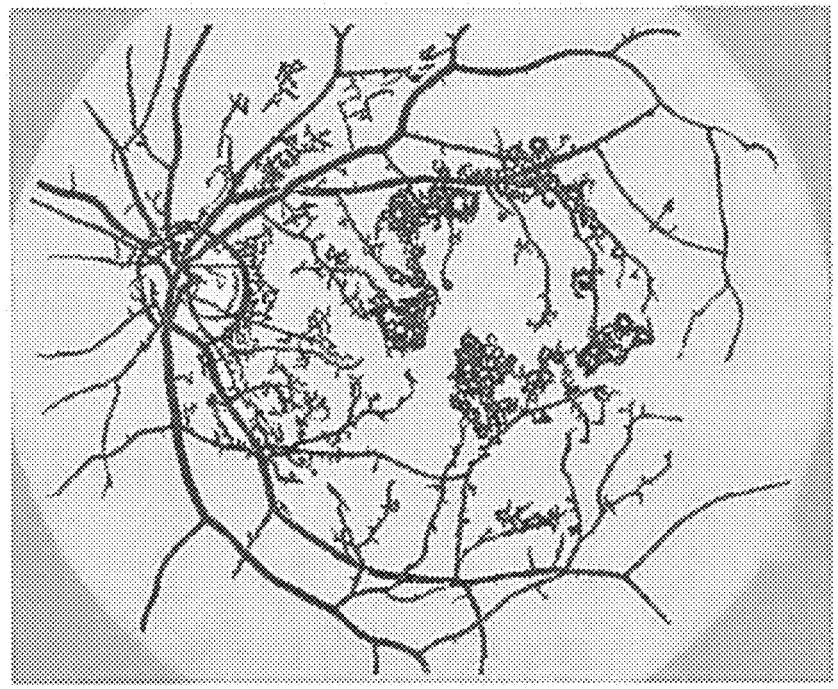
FIGS. 26A-26B. Images showing Floresecien Angiography of Retinopathy (FAR) of a patient having PDR.
Figure 26B:
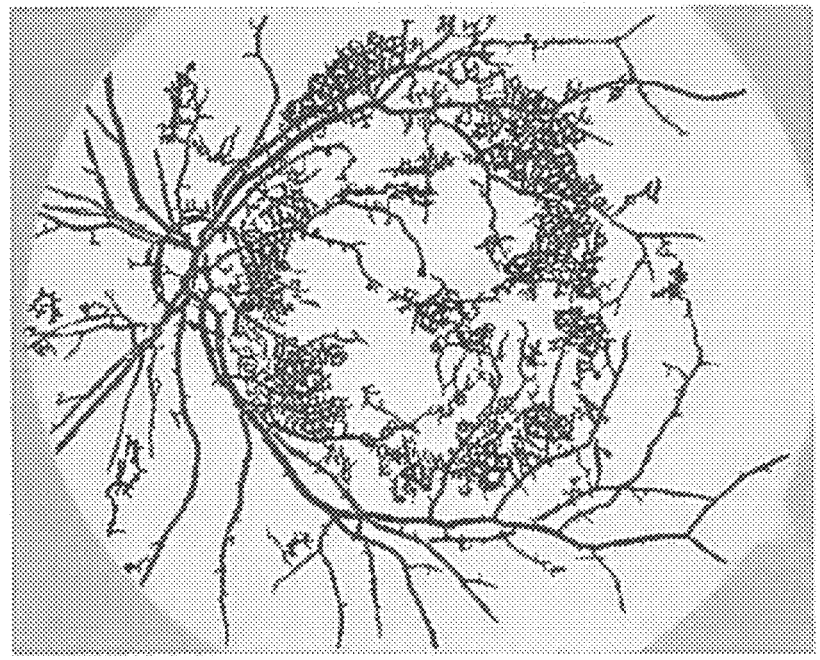

It is to be noted that the results achieved in FIGS. 25A-25C (due to Machine Learning implementation achieved in FIG. 8 and FIG. 16) are comparable to results achieved via Florescien Angiography of Retinopathy, as show in Comparative FIGS. 26A-26B.

Figure 27:
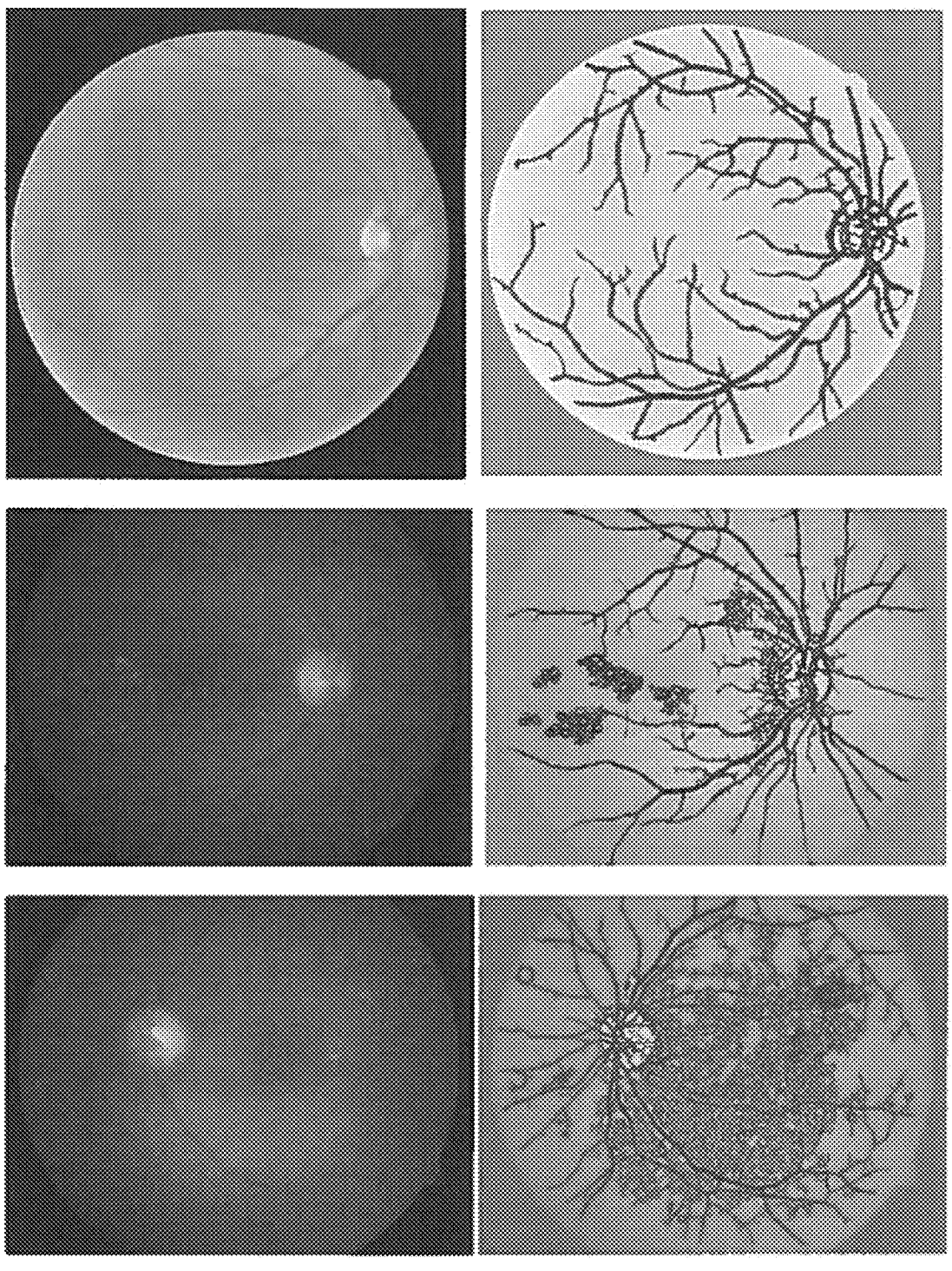
FIG. 27. Additional fundus images and processing results.

FIG. 27 illustrates more examples.

The use of adaptive processing for mask generation and three features, namely, contrast in 0°, contrast in 90° and lacunarity considering foreground pixels resulted in a classification accuracy of 97.2% using ANN and 98.1% with SVM. The results of classification for Example 2 are shown in Table 3.

TABLE 3

Classification accuracy and sensitivity for Experiment 2

| Type of classifier | Classification accuracy (%) | Sensitivity (%) |
|---|---|---|
| ANN | 97.2 | 97 |
| SVM | 98.1 | 99 |

Analysis of the Examples

Modelling the input color fundus image by a Gaussian model based on the intensity profile provides a reliable method of segmenting the retinal vasculature. The first order features do not provide reliable data for classification of diabetic retinopathy. Due to the nature of processed images, textural features give the necessary description that aids in robust classification. The shape features emphasized the severity of the disease.

Figure 28:
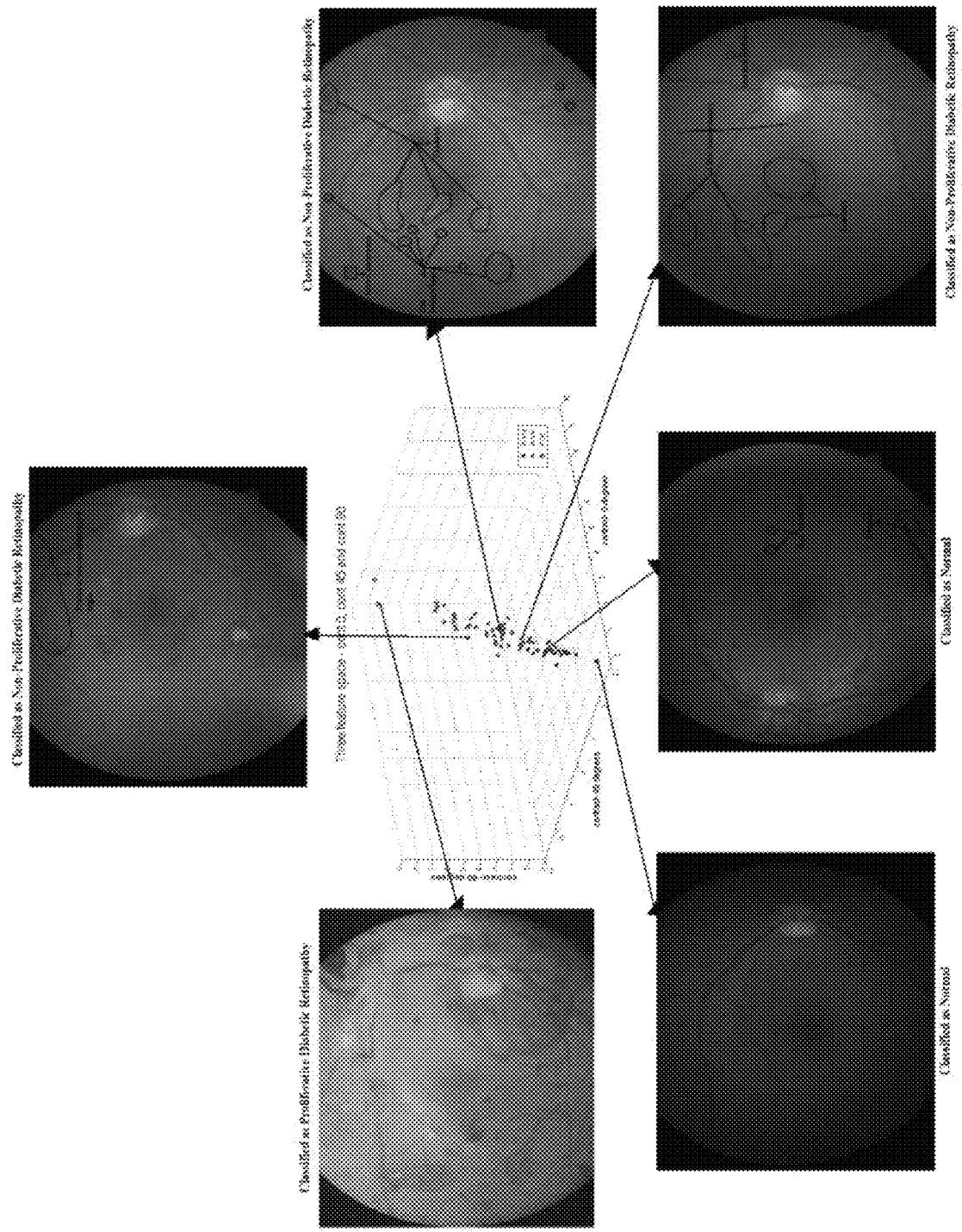
FIG. 28. Different classes of retinopathy in conjunction with a feature space.

The complexity of the research arises due to the fact that it is a three class classification problem instead of a simple binary classification. This means that the problem at hand is highly stochastic in nature. Also, there is a tradeoff including additional samples to the existing feature space. The progression of the disease from the normal or healthy stage to the NPDR stage and further into the PDR stage is represented by a complex feature space that poses a problem of misclassification. The progression of the retinopathy in association with the three dimensional feature space is shown in FIG. 28.

Example 1 utilized a combination of these features that provided a classification accuracy of 93% using SCM. This is an improvement compared to prior methods (Lee et al. Archives of Ophthalmology Col. 123, No. 6, pp. 759-764, 2005), which demonstrated a classification accuracy of 82.6% for normal and NPDR and 88.3% for PDR. In a different prior method, Nayak et al. (Journal of Medical Systems, vo. 32, No. 2, pp. 107-115, 2008) achieved an accuracy of 93% with sensitivity of 90% and specificity of 100%.

As now described herein, the adaptive mask generation approach provides segmentation of blood vessels on an input driven basis. It ensures that the vessels were detected right up to the edge of the input fundus image. This adaptive processing enables selection of the standard deviation of the Gaussian kernel according to the color fundus image. Based on the results of the feature ranking by class separability criteria three features—contrast in 0°, contrast in 90° and lacunarity considering foreground pixels are ranked higher compared to the other features. The approach utilized in Example 2 results in a classification accuracy of 98.1% using the SVM.

Figure 29:
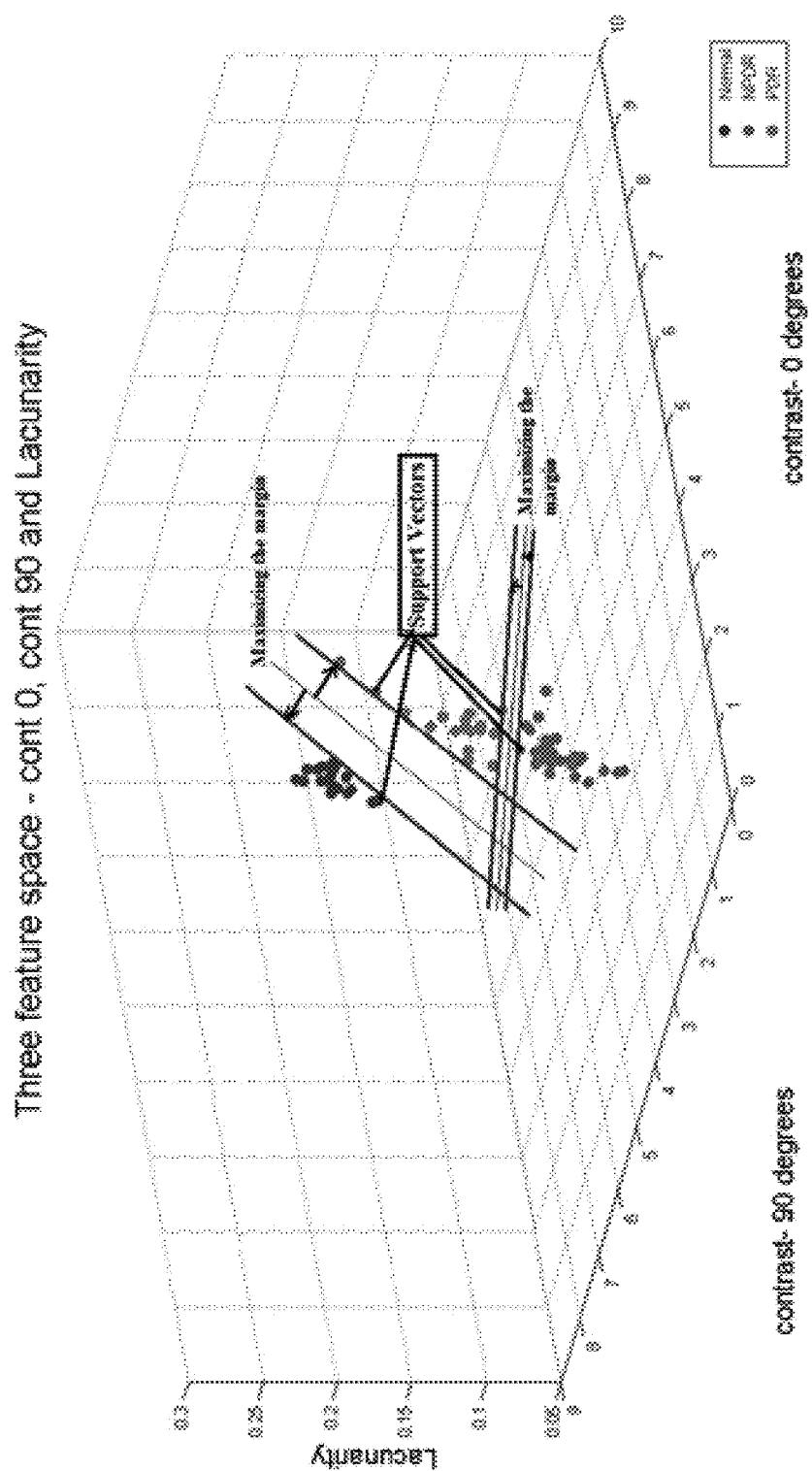
FIG. 29. 3-D feature subspace indicating support vectors and decision boundary.

FIG. 29 illustrates the linear SVM classifier maximizes the margin of the decision boundary in the given feature space.

This is higher than the results obtained by Mookiah et al. (Knowledge-bases Systems, Vo. 39, pp. 9-22, 2013). Table 4 summarizes the comparison of results from the invention described herein approach to those developed in the listed prior methods.

TABLE 4

Comparative Study of Diabetic Retinopathy Detection for Three Class Classification Problem

| Researchers | Features | Methods | Salient Feature/s | Performance Measure |
|---|---|---|---|---|
| Lee et al., Archives of Ophthalmology 123: 759-964 (2005) | HEM, MA, exudates and CWS | NN | High reproducibility | Normal - 82.60%, NPDR - 82.60% PDR - 88.30% |
| Nayak et al., J. Medical Systems, 32: 1-7-115 (2008) | Exudates, area of blood vessel and contrast | NN | Texture and morphological features | Sensitivity - 90% Specificity - 100% Accuracy - 93% |
| Mookiah et al., Knowledge-based | Blood vessels and exudates area, bifurcation points, | GA Optimized | PNN tuning by GA and Particle Swarm | Sensitivity - 96.27% Specificity - 96.08% |

TABLE 4-continued

Comparative Study of Diabetic Retinopathy Detection for Three Class Classification Problem

| Researchers | Features | Methods | Salient Feature/s | Performance Measure |
|---|---|---|---|---|
| System, 39: 9-22 (2013) | global texture and entropies | PNN classifier | Optimization (PSO) | Accuracy - 93% |
| Experiment #1 | Textural contrast in four orientations, fractal dimension and two values of lacunarity | NN and SVM | All anomalies considered - MA, CWS, hemorrhages, exudates and neovascularization; With a fixed mask | NN: Sensitivity - 93% Accuracy - 91.7% SVM: Sensitivity - 97% Accuracy - 93% |
| Experiment #2 | Contrast in 0° and 90° and lacunarity considering foreground pixels only | NN and SVM | All anomalies considered - MA, CWS, hemorrhages, exudates and neovascularization; Adaptive mask generation procedure utilized | NN: Sensitivity - 97% Accuracy - 97.2% SVM: Sensitivity - 99% Accuracy - 98.1% |

Thus, described herein are devices and methods to automate the detection of diabetic retinopathy from digital color fundus images, where various major anomalies are a manifestation of either rupturing of the blood vessels or growth of excess vessels. The textural contrast features provide a description of how pixels are spatially interrelated in different directions. Fractal features describe the shape of the profile, and also characterize the presence of different lesions or spots in the image.

Example 1 utilizes the entire set of seven features, whereas Example 2 uses the various essential features based on feature ranking technique. In both cases, it is now demonstrated herein that a combination of the two sets of features is useful for robust classification that is rotation invariant, translation invariant and scaling invariant. In addition, the use of adaptive mask generation for local entropy thresholding makes the system flexible to any retinal fundus image.

The research provides a comprehensive approach in terms of machine learning by conducting classification using two learning techniques. Also, the classification accuracy attained using both ANN and SVM are comparable to and better than the results of other methods implemented in the literature.

Examples of Devices

Non-limiting examples of devices include using microcontrollers and digital image processors. These devices are especially useful in electronic health systems in order to aid ophthalmologists as an effective diagnostic tool. These devices are especially useful as a principle screening method in less advanced counties allowing sophisticated diagnosis to be made available via digital photographs taken in remote areas to identify those at risk.

These devices/methods are also useful to identify early vessel changes before they could be detected by the human eye. In addition, these devices/methods are useful to form the basis for a multi-sensory data fusion model in order to monitor diabetes. These devices/methods are also useful to identify only the abnormalities in the fundus image based on homomorphic filtering techniques.

These devices/methods are also useful for determining sub-types of NPDR (mild and moderate NPDR) for classification.

These devices/methods are also useful for checking the correlation of blood glucose levels with the progression of diabetic retinopathy.

Figure 30:
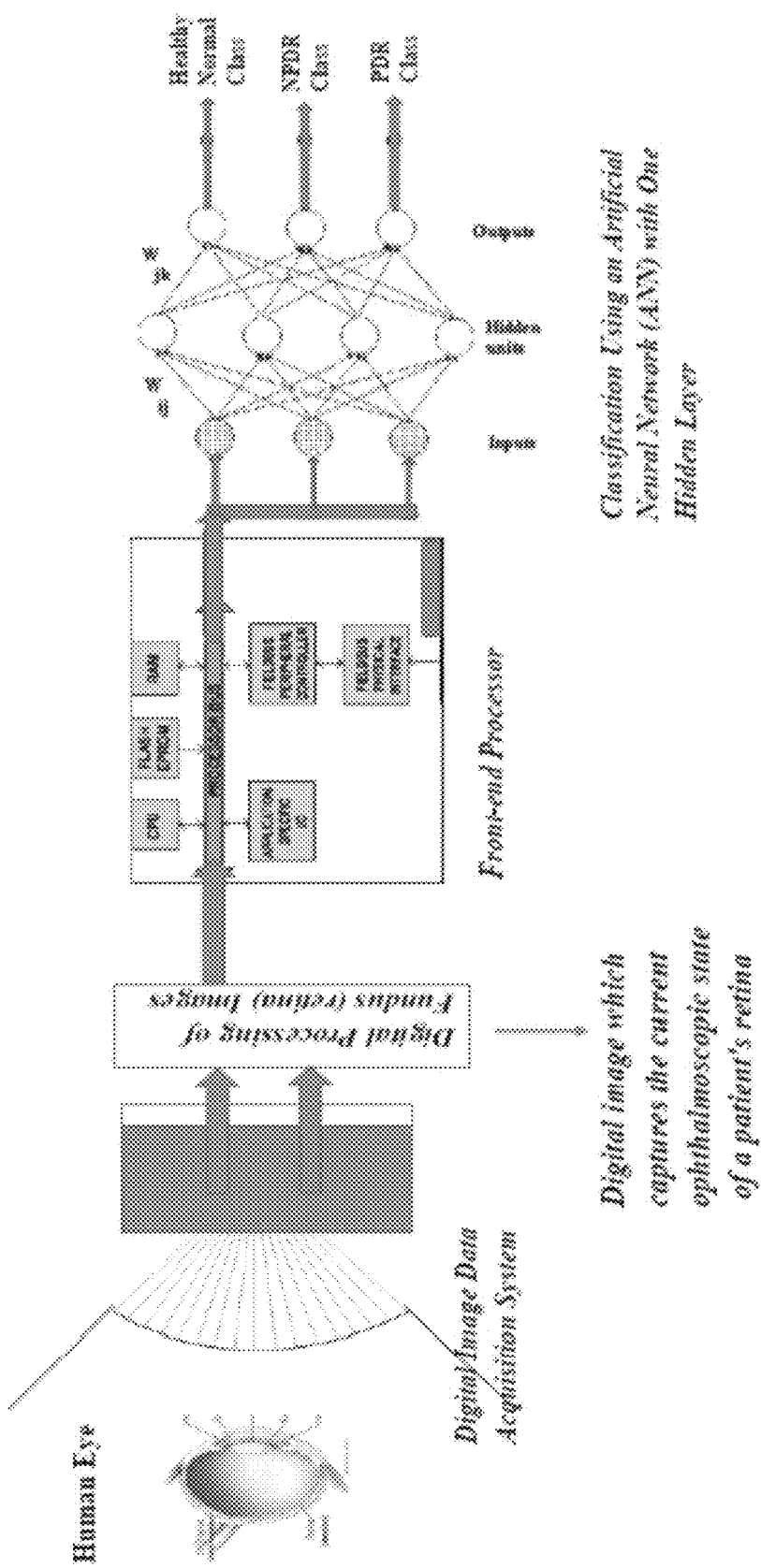
FIG. 30. Block diagram showing one configuration of such a suitable device of an automated computer classifier of diabetic retinopathy and macular degeneration System (ANN).

FIG. 30 is a block diagram showing one configuration of such a suitable device of an automated computer classifier for a diabetic retinopathy and macular degeneration system (ANN), where the following are depicted: human eye; a digital image data acquisition system to provide a digital image which captures the current ophthalmoscope state of a patient's retina; a front-end processor for the digital processing of fundus (retina) images including, for example, a processor bus operatively connected to a CPU, application-specific I/O, flash EPROM, RAM, Field bus peripheral controller, fieldbus physical interface; and illustrating the classification using an artificial neural network (ANN) with one hidden layer.

Figure 31:
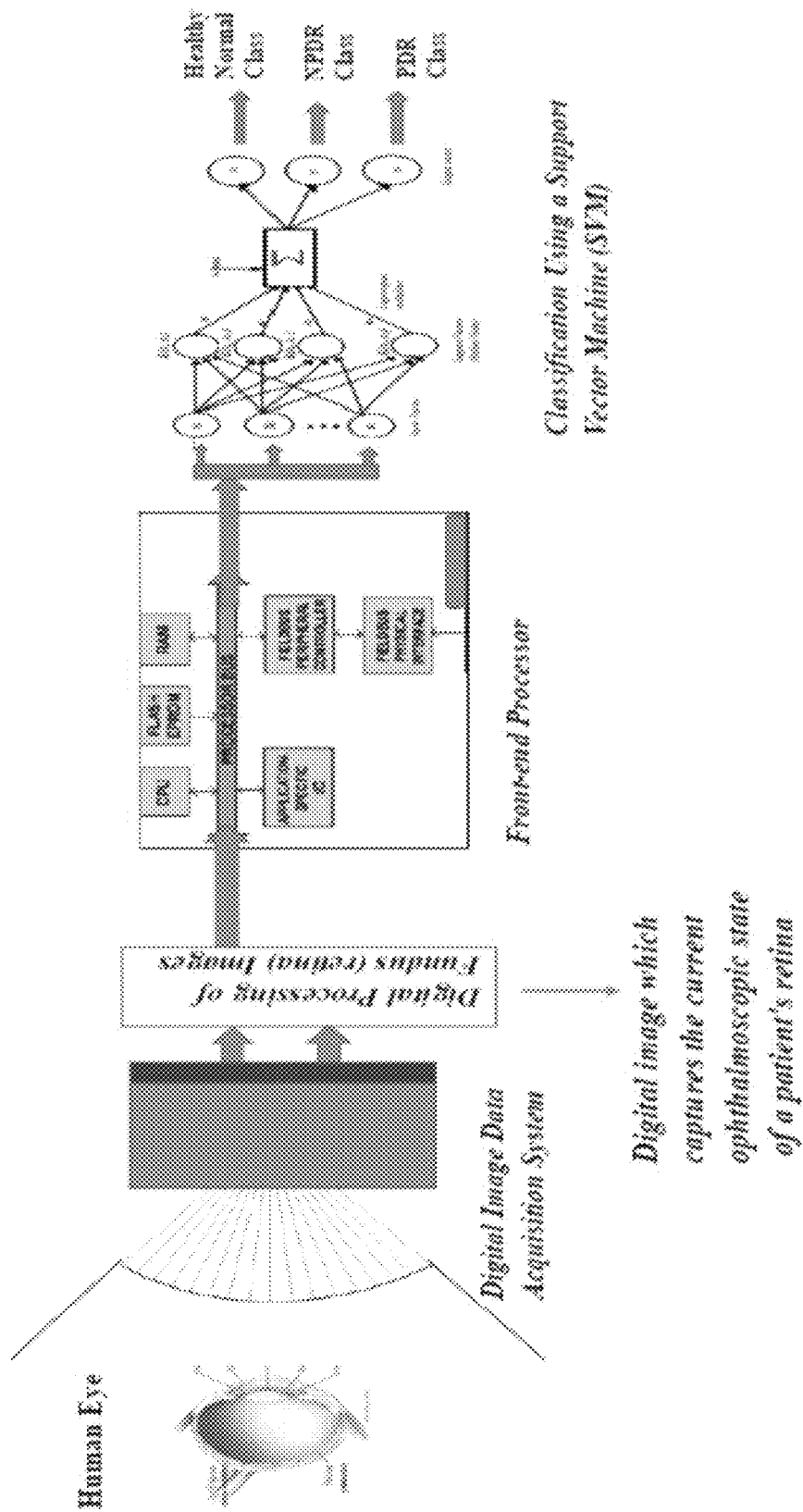
FIG. 31. Block diagram showing one configuration of such a suitable device of an automated computer classifier of diabetic retinopathy and macular degeneration System (USM).

FIG. 31 is a block diagram showing one configuration of such a suitable device of an automated computer classifier for a diabetic retinopathy and macular degeneration system (VSM), where the following are depicted: human eye; a digital image data acquisition system to provide a digital image which captures the current ophthalmoscope state of a patient's retina; a front-end processor for the digital processing of fundus (retina) images including, for example, a processor bus operatively connected to a CPU, application-specific I/O, flash EPROM, RAM, Field bus peripheral controller, fieldbus physical interface; and illustrating the classification using a support vector machine (VSM).

FIG. 30 and FIG. 31 show a system hardware configuration where the front end processors, ANN, and SVN are implementable in a Field Programmable Gate Array (FPGA) or Application Specific Integrated Circuit (ASIC); thus, allowing the aforementioned algorithms to be implemented low-cost mature technology hardware.

Non-Limiting Example of Code

Pseudo Code

Segmentation of retinal vasculature
1. Start
2. Read color fundus image and convert to grayscale
3. Determine size of image
4. Call to function that performs Gaussian filtering
    a. For i = 1 to row_number
        i. For j = 1 to column-number
            1. Calculate impulse response for length, L − 9
            2. Convolve impulse response with input -continued 3. Elicit maximum response and store
        4. Rotate image
    ii. End
  b. End
  c. Store result as output_stage1
5. Call to function that performs local entropy thresholding
  a. Calculate GLCM for output_stage1I
  b. Compute probability of co-occurrence
  c. Divide outpu1-stage1 into foreground and background
  d. Calculate entropies Hf and Hb
  e. Compute optimum threshold
6. Call to function that generates mask
  a. Fixed mask for Example 1 or
  b. Calculate standard deviation for input image and based on standard deviation value determine mask
7. Based on mask and threshold value, convert image to binary using imbw
8. Blood vessel edge profile image J obtained
9. Stop
Feature Extraction
1. Start
2. Read blood vessel edge profile
3. Calculate GLCM for 0°, 45°, 90° and 135°
4. Calculate respective probabilities of co-occurrences
5. Calculate contrast for 0°, 45°, 90° and 135°
6. Calculate fractal dimension by box-count method and two values of lacunarity using FracLac toolbox in ImageJ
7. Store features as a matrix
8. Stop
Classification
1. Start
2. Initialize dataset to be features
3. Label dataset into respective classes
4. For i = 0.1 to 0.9
  a. Divide dataset into training and testing by cross-validation using hold-out parameter i.
  b. Classify, using ANN and SVM
  c. Obtain classification accuracy
  d. End
5. Average classification accuracy
6. Stop Non-Limiting Examples of Electronic Apparatus Readable Media, Systems, Arrays and Methods of Using the Same A "computer readable medium" is an information storage media that can be accessed by a computer using an available or custom interface. Examples include memory (e.g., ROM or RAM, flash memory, etc.), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

The system can also include detection apparatus that is used to detect the desired information, using any of the approaches noted herein. For example, a detector configured to obtain and store retinal images or a retinal reader can be incorporated into the system. Optionally, an operable linkage between the detector and a computer that comprises the system instructions noted above is provided, allowing for automatic input of specific information to the computer, which can, e.g., store the database information and/or execute the system instructions to compare the detected specific information to the look up table.

Optionally, system components for interfacing with a user are provided. For example, the systems can include a user viewable display for viewing an output of computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Sequel™, Oracle™, Paradox™) can be adapted to the present invention. For example, the systems can include software having the appropriate character string information, e.g., used in conjunction with a user interface (e.g., a GUI in a standard operating system such as a Windows, Macintosh or LINUX system) to manipulate strings of characters. Specialized sequence alignment programs such as BLAST can also be incorporated into the systems of the invention.

As noted, systems can include a computer with an appropriate database. Software, as well as data sets entered into the software system comprising any of the images herein can be a feature of the invention. The computer can be, e.g., a PC (Intel x86 or Pentium chip-compatible DOS™, OS2™, WINDOWS™, WINDOWS NT™, WINDOWS95™, WINDOWS98™, WINDOWS2000, WINDOWSME, or LINUX based machine, a MACINTOSH™, Power PC, or a UNIX based (e.g., SUN™ work station or LINUX based machine) or other commercially common computer which is known to one of skill Software for entering and aligning or otherwise manipulating images is available, e.g., BLASTP and BLASTN, or can easily be constructed by one of skill using a standard programming language such as Visualbasic, Fortran, Basic, Java, or the like.

In certain embodiments, the computer readable medium includes at least a second reference profile that represents a level of at least one additional retinal image from one or more samples from one or more individuals exhibiting indicia of diabetic and/or macular degeneration.

In another aspect, there is provided herein a computer system for determining whether a subject has, or is predisposed to having, diabetic and/or macular degeneration, comprising a database and a server comprising a computer-executable code for causing the computer to receive a profile of a subject, identify from the database a matching reference profile that is diagnostically relevant to the individual profile, and generate an indication of whether the individual has, or is predisposed to having, diabetic and/or macular degeneration.

In another aspect, there is provided herein a computer-assisted method for evaluating the presence, absence, nature or extent of diabetic and/or macular degeneration in a subject, comprising: i) providing a computer comprising a model or algorithm for classifying data from a sample obtained from the individual, wherein the classification includes analyzing the data for the presence, absence or amount of at least measured feature; ii) inputting data from the image sample obtained from the individual; and, iii) classifying the image to indicate the presence, absence, nature or extent of diabetic and/or macular degeneration.

As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM, and the like; and general hard disks and hybrids of these categories such as magnetic/optical storage media. The medium is adapted or configured for having recorded thereon a marker as described herein.

As used herein, the term "electronic apparatus" is intended to include any suitable computing or processing apparatus or other device configured or adapted for storing data or information. Examples of electronic apparatus suitable for use with embodiments of the present invention include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems.

As used herein, "recorded" refers to a process for storing or encoding information on the electronic apparatus readable medium. Those skilled in the art can readily adopt any method for recording information on media to generate materials comprising the markers described herein.

A variety of software programs and formats can be used to store the image information on the electronic apparatus readable medium. Any number of data processor structuring formats (e.g., text file or database) may be employed in order to obtain or create a medium having recorded thereon the markers. By providing the markers in readable form, one can routinely access the information for a variety of purposes. For example, one skilled in the art can use the information in readable form to compare a sample image with the control information stored within the data storage means.

Thus, there is also provided herein a medium for holding instructions for performing a method for determining whether a subject has diabetic and/or macular degeneration or a pre-disposition for developing diabetic and/or macular degeneration, wherein the method comprises the steps of: i) determining the presence or absence of certain features in retinal images, and based on the presence or absence of such features; ii) determining whether the individual has diabetic and/or macular degeneration or a pre-disposition for developing diabetic and/or macular degeneration, and/or iii) recommending a particular treatment for diabetic and/or macular degeneration or pre-diabetic and/or macular degeneration condition.

It is contemplated that different entities may perform steps of the contemplated methods and that one or more means for electronic communication may be employed to store and transmit the data. It is contemplated that raw data, processed data, diagnosis, and/or prognosis would be communicated between entities which may include one or more of: a primary care physician, patient, specialist, insurance provider, foundation, hospital, database, counselor, therapist, pharmacist, and government.

There is also provided herein an electronic system and/or in a network, a method for determining whether a subject has diabetic and/or macular degeneration or a pre-disposition for developing diabetic and/or macular degeneration, wherein the method comprises the steps of: i) determining the presence or absence of certain features in retinal images, and based on the presence or absence of such features; ii) determining whether the individual has diabetic and/or macular degeneration or a pre-disposition for developing diabetic and/or macular degeneration; and/or, iii) recommending a particular treatment for diabetic and/or macular degeneration or pre-diabetic and/or macular degeneration condition. The method may further comprise the step of receiving information associated with the individual and/or acquiring from a network such information associated with the individual.

Also provided herein is a network, a method for determining whether a subject has diabetic and/or macular degeneration or a pre-disposition for developing diabetic and/or macular degeneration associated with certain features in retinal images, the method comprising the steps of: i) receiving information associated with the retinal images, ii) acquiring information from the network corresponding to retinal images and/or diabetic and/or macular degeneration, and based on one or more of the retinal images and the acquired information, iii) determining whether the individual has diabetic and/or macular degeneration or a pre-disposition for developing diabetic and/or macular degeneration. The method may further comprise the step of recommending a particular treatment for the diabetic and/or macular degeneration or pre-diabetic and/or macular degeneration disease condition.

Systems

Particular embodiments are directed to systems useful for the practice of one or more of the methods described herein. Systems for using detection method described herein for therapeutic, prognostic, or diagnostic applications and such uses are contemplated herein. The systems can include devices for capturing retinal images, as well as information regarding a standard or normalized profile or control.

Also, the systems can generally comprise, in suitable means for image collecting, devices for each individual retinal image. The kit can also include instructions for employing the kit components as well the use of any other materials not included in the kit. Instructions may include variations that can be implemented. It is contemplated that such reagents are embodiments of systems of the invention. Also, the systems are not limited to the particular items identified above and may include any reagent used for the manipulation or characterization of the retinal images and/or data derived therefrom.

The systems described herein can reduce the costs and time associated collecting a variety of images. The systems may be used by research and commercial laboratories and medical end users to facilitate collection of retinal data in remote locations.

The device and computing system can be configured to process a plurality of images obtained from a single patient imaging session or encounter. Further, it is to be understood that the computing system can be further configured to operate in a telemedicine setting in order to provide clinical health care at a distance. Use of the devices and methods described herein help eliminate distance barriers and can improve access to medical services that would often not be consistently available in distant rural communities, and to receive a request for an analysis from a remote computing system that is in a different geographic location than the computing system.

In certain embodiments, the central processing unit is remotely located from the retinal scanner. In other embodiments, the central processing unit and the retinal scanner can be integrated together in a physical structure (often including a computer and a display screen) that displays information (for example, a booth or kiosk in a physician's office, or in a commercial setting such as a shopping area, airport, or other public place.

The computing system can be used in the classification of different abnormalities or diseases and to use the set of classifiers to ascertain presence, absence or severity of plurality of diseases, abnormalities, or lesions. It is to be understood that the devices and methods described herein are useful for the detection of a plurality of diseases including such non-limiting examples as: diabetic retinopathy, cytomegalovirus retinitis, retinopathy of prematurity, clinical myopia, hypertensive retinopathy, stroke, cardiovascular disease, glaucoma, macular degeneration, Alzheimer's, or macular edema.

It is also to be understood that the analysis of the retinal image can further include detecting and excluding a non-pathological anatomical feature from the retinal image. Also, it is to be understood that the analysis of the retinal image can be limited to a prescribed region of the retinal image, or to a random selection of pixels from the retinal image.

It is further to be understood that the detection of an abnormality can include the gathering of additional data. Non-limiting examples include: demographic information, age data, body mass index data, blood pressure data, genetic information, family history data, race data, ocular information, glucose level, ocular pressure, artero/venous ratio, systemic factors, and the like.

In a particular embodiment, a computing system can include: one or more hardware computer processors; and one or more storage devices configured to store software instructions configured for execution by the one or more hardware computer processors in order to cause the computing system to: 1) determine the presence or absence of a set of features in at least one retinal image taken from the subject by: i) creating an edge profile map of the fundus images that detects the retinal vasculature and one or more abnormalities characteristic of the type of retinopathy based on an adaptive mask generation procedure; and ii) classifying the processed images using features which describe the texture and shape via artificial neural network (ANN) and support vector machines (SVM); 2) and, based on the presence or absence of such set of features, 3) determine whether the subject has diabetic and/or macular degeneration, or a pre-disposition for developing diabetic and/or macular degeneration; 4) optionally, recommend a particular treatment for diabetic and/or macular degeneration or pre-diabetic and/or macular degeneration condition.

It is also to be understood that the device described herein can be a non-transitory computer storage that stores executable program instructions that, when executed by one or more computing devices, configures the one or more computing devices to perform the operations described herein.

It is also to be understood that the device described herein can be a non-transitory computer-readable medium that stores executable instructions for execution by a computer having memory where the medium storing instructions for carrying out the methods described herein.

In one embodiment, the device can include a retinal scanner constructed to obtain retinal data, and a central processing unit (CPU) in communication with the retinal scanner. The CPU can include memory-storable CPU-executable instructions for detecting retinal abnormalities.

The CPU can perform the following in response to receiving retinal data based on the memory-storable CPU-executable instructions: a formation of a retinal image based on the retinal data; an analysis of the retinal image, wherein the analysis comprises: determining the presence or absence of a set of features in at least one retinal image taken from the subject by: i) creating an edge profile map of the fundus images that detects the retinal vasculature and one or more abnormalities characteristic of the type of retinopathy based on an adaptive mask generation procedure; and ii) classifying the processed images using features which describe the texture and shape via artificial neural network (ANN) and support vector machines (SVM); and, based on the presence or absence of such set of features, determining whether the subject has diabetic and/or macular degeneration, or a pre-disposition for developing diabetic and/or macular degeneration; optionally, recommending a particular treatment for diabetic and/or macular degeneration or pre-diabetic and/or macular degeneration condition.

The methods and systems of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method for determining a propensity to develop diabetic retinopathy, and/or macular degeneration in a subject, comprising:
   a) measuring a set of 3-dimensional features in a captured retinal image of the subject by using:
      i) a segmentation step of retinal vasculature and blood vessel edge profiling;
      ii) a feature extraction step that measures:
         contrast in 0°, and 90° orientations,
         lacunarity considering foreground pixels only, and
         lacunarity considering foreground and background pixels;
      iii) a classification step using a three-layer neural network;
   b) comparing the set of the 3-dimensional features measured in step (a) relative to a set of 3-dimensional features in control retinal images, and
   c) determining the risk for developing diabetic retinopathy and/or macular degeneration being relatively high in the subject where there are differences between the subject retina as compared to the control retinal images.

2. The method of claim 1, further including indicating when a therapeutic intervention aimed at decreasing the incidence of diabetes is beneficial.

3. The method of claim 1, wherein the segmentation step a) i) includes calculating a two-dimensional Gaussian kernel of the blood vessels in the retinal image.

4. The method of claim 1, comprising correlating the measured 3-dimensional features data of step b) with similar data of control retinal images from a reference population.

5. The method of claim 1, wherein the captured retinal image of step a) is a grayscale image, denoted as $I_g(n_1, n_2)$ is subjected to a local thresholding scheme based on entropy, and a mask $M(n_1, n_2)$ is generated in order to define the Region of Interest (ROI) for application of thresholding, the mask generated being a linear convolution between the system impulse response and the input grayscale image, and the mask being determined depending on the grayscale input image, I ($n_1$, $n_2$).

6. The method of claim 1, wherein the retinal image is a color fundus image, and step a) i) comprises determining the presence or absence of a set of features in at least one color fundus image taken from the subject comprises:
   i) creating an edge profile map of the color fundus images that detects the retinal vasculature and one or more abnormalities characteristic of the type of retinopathy based on an adaptive mask generation procedure; and
   ii) classifying the processed color fundus images of step i) using a set of features which describe the texture and shape via artificial neural network (ANN) and/or support vector machines (SVM).

7. The method of claim 1, wherein the three-layer neural network comprises one or more of: an artificial neural network (ANN), and a support vector machine (SVM).

8. The method of claim 1, further comprising:
   correlating the measured 3-dimensional features data of step b) taken from the subject at a first time with measured 3-dimensional features data taken from the subject at a second time; and,
   distinguishing normal stage from non-proliferative diabetic retinopathy, the proliferative diabetic retinopathy, and/or macular degeneration in the subject, by comparing the 3-dimensional features determined in step b) taken a the first and second points in time from the same subject.

9. A computer-implemented method for determining whether a subject has diabetic retinopathy and/or macular degeneration, or a pre-disposition for developing diabetic and/or macular degeneration, at least a portion of the method being performed by a computing device comprising at least one processor, the method comprises the steps of:
   i) generating an edge profile map of a fundus image taken from a retina of a subject;
   ii) identifying, after the edge profile is generated, user-provided data about the retinal vasculature and blood vessel edge profiling;
   iii) generating additional user-provided 3-dimensional data by measuring:
      a) contrast in 0°, and 90° orientations,
      b) lacunarity considering foreground pixels only, and
      c) lacunarity considering foreground and background pixels;
   iv) classifying the user-provided 3-dimensional data of steps ii) and iii) using a training module, stored in memory, and
   v) generating a prediction whether a subject has diabetic and/or macular degeneration, or a pre-disposition for developing diabetic and/or macular degeneration using the classification data of step iv) as input to a machine-learning algorithm that outputs the predication.

10. The computer-implemented method of claim 9, wherein the training module includes a three-layer neural network for classifying the user-provided data via an artificial neural network (ANN) and/or a support vector machine (SVM).

11. The computer-implemented method of claim 9, wherein the prediction further includes a recommendation for a particular treatment for diabetic and/or macular degeneration or pre-diabetic and/or macular degeneration condition.

12. A method comprising, at a network management server,
   receiving an edge profile map of a fundus image taken from a retina of a subject from a retinal scanning device;
   identifying, after the edge profile is generated, user-provided data about the retinal vasculature and blood vessel edge profiling;
   generating additional user-provided 3-dimensional data by measuring:
   contrast in 0°, and 90° orientations,
   lacunarity considering foreground pixels only, and
   lacunarity considering foreground and background pixels;
   classifying the user-provided 3-dimensional data additional user-provided data using a training module, stored in memory, and
   generating a prediction whether a subject has diabetic and/or macular degeneration, or a pre-disposition for developing diabetic and/or macular degeneration using the classification data of step iv) as input to a machine-learning algorithm that outputs the predication.

13. The method of claim 12, including communicating information about the prediction to a network client device.

* * * * *

UNITED STATES PATENT AND TRADEMARK OFFICE
CERTIFICATE OF CORRECTION

PATENT NO. : 10,722,115 B2
APPLICATION NO. : 15/751947
DATED : July 28, 2020
INVENTOR(S) : Mehmet Celenk et al.

Page 1 of 1

It is certified that error appears in the above-identified patent and that said Letters Patent is hereby corrected as shown below:

In the Specification

Column 1, STATEMENT REGARDING FEDERALLY FUNDED RESEARCH, Line 27, please correct from:
"This invention not was made" to --This invention was not made--

Column 2, SUMMARY OF THE INVENTION, Line 34, please correct from:
"specifically ANNs and SVNs)" to --specifically ANNs and SVMs)--

Column 2, BRIEF DESCRIPTION OF THE DRAWINGS, Line 56, please correct from:
"FIG.  6." to --FIG. 6.--

Column 3, BRIEF DESCRIPTION OF THE DRAWINGS, Line 51, please correct from:
"(USM)." to --(SVM).--

Signed and Sealed this
Tenth Day of November, 2020

Andrei Iancu
*Director of the United States Patent and Trademark Office*